United States Patent [19]
Gellman et al.

[11] Patent Number: 6,042,534
[45] Date of Patent: Mar. 28, 2000

[54] STABILIZATION SLING FOR USE IN MINIMALLY INVASIVE PELVIC SURGERY

[75] Inventors: Barry N. Gellman, Easton; William Martin, Franklin, both of Mass.; Raymond Rackley, Shaker Heights, Ohio

[73] Assignee: SCIMED Life Systems, Inc., Maple Grove, Minn.

[21] Appl. No.: 09/023,398

[22] Filed: Feb. 13, 1998

Related U.S. Application Data

[60] Provisional application No. 60/038,379, Feb. 13, 1997.

[51] Int. Cl.[7] .................................................. A61F 2/02
[52] U.S. Cl. ................................................................. 600/30
[58] Field of Search .............................. 600/300, 30, 29, 600/37; 606/151; 128/898, 897

[56] References Cited

U.S. PATENT DOCUMENTS

| | | |
|---|---|---|
| 2,671,444 | 3/1954 | Pease . |
| 3,054,406 | 9/1962 | Usher . |

(List continued on next page.)

FOREIGN PATENT DOCUMENTS

| | | |
|---|---|---|
| 0599772 A1 | 6/1994 | European Pat. Off. . |
| 6-114067 | 4/1994 | Japan . |
| 503 271 | 4/1996 | Sweden . |
| 506 164 | 11/1997 | Sweden . |
| 2268690 | 1/1994 | United Kingdom . |
| WO 88/01853 | 3/1988 | WIPO . |
| WO 92/16152 | 10/1992 | WIPO . |
| WO 93/10715 | 6/1993 | WIPO . |
| WO 93/10731 | 6/1993 | WIPO . |
| WO 93/19678 | 10/1993 | WIPO . |
| WO 94/19029 | 9/1994 | WIPO . |
| WO 94/28799 | 12/1994 | WIPO . |
| WO 96/06567 | 3/1996 | WIPO . |
| WO 97/13465 | 4/1997 | WIPO . |
| WO 97/30638 | 8/1997 | WIPO . |
| WO 97/43982 | 11/1997 | WIPO . |
| WO 98/12971 | 4/1998 | WIPO . |
| WO 98/35632 | 8/1998 | WIPO . |

OTHER PUBLICATIONS

Kovac et al., Public Bone Suburethral Stabilization Sling For Recurrent Urinary Incontinence, Obstetrics & Gynecology, pp. 624–627, Apr. 1997.

Araki et al., The Loop–Loosening Procedure For Urination Difficulties After Stamey Suspension Of The Vesical Neck, J. Urology 144: 319–323 (1990).

Beck et al., A 25–Year Experience With 519 Anterior Colporrhaphy Procedures, Obstetrics and Gynecology 78: 1011–1018 (1991).

Cruikshank et al., Anterior vaginal wall culdeplasty at vaginal hysterectomy to prevent posthysterectomy anterior vaginal wall prolapse, Am. J. Obstetrics and Gynecology 174: 1863–1872 (1996).

Hoffman et al., Transvestibular Retropubic Bladder Neck Suspension: A pilot study, J. Reproductive Med. 40: 181–184 (1995).

(List continued on next page.)

*Primary Examiner*—Samuel G. Gilbert
*Attorney, Agent, or Firm*—Testa, Hurwitz & Thibeault, LLP

[57] ABSTRACT

The present invention relates to prefabricated urethral suspension slings, methods of making the slings, methods of attaching suture to the slings, kits comprising the slings, and methods of using the slings to treat urinary incontinence. The slings comprise a biocompatible material having an elongate shape adapted for urethral suspension. The material has a central portion extending longitudinally between a first end portion and a second end portion. Each end portion of the sling contains at least one suture receiving site. The suture receiving sites are formed prior to surgery and may be reinforced through a variety of means. Sutures may be attached to the suture receiving sites during the manufacturing process or by the physician prior to or during surgery. Additionally, the end portions of the sling containing the suture receiving sites may be thicker than the central portion of the sling.

19 Claims, 14 Drawing Sheets

U.S. PATENT DOCUMENTS

| | | | |
|---|---|---|---|
| 3,580,313 | 5/1971 | McKnight | 145/46 |
| 3,705,575 | 12/1972 | Edwards . | |
| 3,710,592 | 1/1973 | Scow | 66/1 A |
| 3,744,495 | 7/1973 | Johnson . | |
| 4,085,756 | 4/1978 | Weaver . | |
| 4,172,458 | 10/1979 | Pereyra . | |
| 4,400,833 | 8/1983 | Kurland | 3/1 |
| 4,409,974 | 10/1983 | Freedland . | |
| 4,414,967 | 11/1983 | Shapiro . | |
| 4,452,245 | 6/1984 | Usher . | |
| 4,545,374 | 10/1985 | Jacobson . | |
| 4,549,545 | 10/1985 | Levy . | |
| 4,633,873 | 1/1987 | Dumican et al. . | |
| 4,741,330 | 5/1988 | Hayhurst . | |
| 4,784,126 | 11/1988 | Hourahane . | |
| 4,854,316 | 8/1989 | Davis . | |
| 4,857,041 | 8/1989 | Annis et al. | 600/30 |
| 4,872,451 | 10/1989 | Moore et al. . | |
| 4,873,977 | 10/1989 | Avant et al. . | |
| 4,938,760 | 7/1990 | Burton et al. | 600/29 |
| 4,969,892 | 11/1990 | Burton et al. | 606/218 |
| 4,973,300 | 11/1990 | Wright | 600/37 |
| 4,997,434 | 3/1991 | Seedhom et al. | 606/80 |
| 5,012,822 | 5/1991 | Schwarz . | |
| 5,013,292 | 5/1991 | Lemay | 600/30 |
| 5,019,032 | 5/1991 | Robertson | 600/29 |
| 5,026,398 | 6/1991 | May et al. | 623/13 |
| 5,064,434 | 11/1991 | Haber | 623/11 |
| 5,112,344 | 5/1992 | Petros | 606/148 |
| 5,122,155 | 6/1992 | Eberbach | 606/213 |
| 5,147,374 | 9/1992 | Fernandez | 606/151 |
| 5,149,329 | 9/1992 | Richardson | 604/272 |
| 5,195,542 | 3/1993 | Gazielly et al. | 128/898 |
| 5,252,701 | 10/1993 | Jarrett et al. | 528/354 |
| 5,254,133 | 10/1993 | Seid | 606/215 |
| 5,256,133 | 10/1993 | Spitz | 600/29 |
| 5,258,000 | 11/1993 | Gianturco | 606/151 |
| 5,290,217 | 3/1994 | Campos | 600/37 |
| 5,328,077 | 7/1994 | Lou | 227/175 |
| 5,337,736 | 8/1994 | Reddy . | |
| 5,362,294 | 11/1994 | Seitzinger | 600/37 |
| 5,366,479 | 11/1994 | McGarry et al. | 606/219 |
| 5,368,602 | 11/1994 | De La Torre | 606/151 |
| 5,425,984 | 6/1995 | Kennedy et al. | 428/229 |
| 5,437,603 | 8/1995 | Cerny et al. | 600/29 |
| 5,441,508 | 8/1995 | Grazielly et al. | 606/151 |
| 5,451,235 | 9/1995 | Lock et al. | 606/213 |
| 5,474,543 | 12/1995 | McKay | 604/272 |
| 5,527,341 | 6/1996 | Gogolewski et al. | 606/232 |
| 5,527,342 | 6/1996 | Pietrzak et al. | 606/232 |
| 5,544,664 | 8/1996 | Benderev et al. | 128/898 |
| 5,549,619 | 8/1996 | Peters et al. | 606/151 |
| 5,591,163 | 1/1997 | Thompson | 606/29 |
| 5,611,515 | 3/1997 | Benderev et al. | 128/898 |
| 5,643,288 | 7/1997 | Thompson | 606/139 |
| 5,681,310 | 10/1997 | Yuan et al. | 606/61 |
| 5,690,655 | 11/1997 | Hart et al. | 606/148 |
| 5,697,931 | 12/1997 | Thompson | 606/72 |
| 5,707,647 | 1/1998 | Dunn et al. | 424/443 |
| 5,807,403 | 8/1998 | Beyars et al. | 606/232 |
| 5,816,258 | 10/1998 | Jervis | 128/898 |
| 5,840,011 | 11/1998 | Landgrebe et al. | 600/30 |
| 5,899,909 | 5/1999 | Claren et al. | 606/119 |
| 5,922,026 | 7/1999 | Chin | 623/11 |

OTHER PUBLICATIONS

Mascio et al, Therapy of Urinary Stress Incontinence in Women: using Mitek® GII Anchors, Mitek® Brochure, 1993.

Parra, et al., Experience with a Simplified Technique for the Treatment of Female Stress Urinary Incontinence, British J. Urology 66: 615–617 (1990).

Richmond et al., Modification Of The Bankart Reconstruction With A Suture Anchor: Report Of A New Technique, Am. J. Sports Med. 19: 343–346 (1991).

Trockman et al., Modified Pereyra Bladder Neck Suspension: 10–year mean follow–up using outcomes analysis in 125 patients, J. Urology 154: 1841–1847 (1995).

Petros et al., The Intravagainal Slingpasty Operation, Minimally Invasive Technique for Cure of Urinary Incontinence in the Female, Augt NZJ. Obstet Gynaecol 4:453–461 (1996).

Bayer: A new approach to primary strengthening of colostomy with Marlex® Mesh to prevent paracolostomy hernia, Surgery, gynecology and Obstetrics 163: 579–580 (1986).

Cruikshank: Reconstructive procedures for the gynecologic surgeon, Am. J. Obstetrics and Gynecology 168: 469–475 (1993).

Falconer: Clinical Outcome and Changes in Connective Tissue Metabolism After Intravaginal Slingplasty in Stress Incontinent Women, Int. Urogynecol. J. 7: 133–137 (1996).

Forneret: Cost–effective treatment of female stress urinary incontinence: modified pereyra bladder neck suspension, Urology 25: 365–367 (1985).

Gittes: No–incision pubovaginal suspension for stress incontinence, J. Urology 138: 568–570 (1987).

Hancock: Transpubic suspension of the Bladder Neck for Urinary Incontinence, J. Urology 123: 667–668 (1980).

Kovac: Pubic Bone Suburethral Stabilization Sling for Recurrent Urinary Incontinence, Obstetrics and Gynecology 89:624–627 (1997).

Leach: Percutaneous Bladder Neck Suspension, Urol Clinics of N. Am. 23: 511–516 (1996).

Leach: Bone fixation technique for transvaginal needle suspension, Urology 31: 388–390 (1988).

McKiel: Marshall–Marchetti Procedure: Modification, J. Urology 96: 737–739 (1966).

Pereyra: A Simplified Surgical Procedure for the Correction of Stress Incontinence in Women, West. J. Surg. Obstetrics and Gynecology: 223–226 (1959).

Petros: The Intravaginal Slingplasty Operation, a Minimally Invasive Technique for Cure of Urinary Incontinence in the Female, Aust. NZ 1. Obstet. Gynaecol. 36: 453–461 (1996).

Petros: Ambulatory Surgery of urinary incontinence and vaginal prolapse, Med. J. Aust. 161: 171–172 (1994).

Raz: Modified Bladder Neck Suspension for Female Stress Incontinence, Urology 17: 82–85 (1981).

Schaeffer: Endoscopic suspension of visical neck for urinary incontinence, Urology 23:484–494 (1984).

Scheuer: The Modified Pereyra Bladder Neck Suspension Procedure: Using Mike GII Anchors, Mitek® Brochure (1993).

Spencer: A comparison of Endoscopic suspension of the vesical neck with suprapubic vesicourethropexy for treatment of stress urinary incontinence, J. Urology 137: 411–415 (1987).

Stamey: Endoscopic Suspension of the Vesical Neck for Urinary Incontinence in Females: Report on 203 Consecutive patients, Ann. Surg. 192: 465–471 (1980).

Stamey: Endoscopic Suspension of the vesical neck for urinary incontinence, Surgery, Gynecology and Obstetrics 136: 547–554 (1973).

Ulmsten: An Ambulatory Surgical Procedure Under Local Anesthesia for Treatment of Female Urinary Incontinence, Int. Urogynecol. J. 7: 81–86 (1996).

Ulmsten: Intravaginal Slingplasty (IVS): An Ambulatory Surgical Procedure for Treatment of Female Urinary Incontinence Scand. J. Urol. Nephrol 29: 75–82, (1995).

Webster: Voiding dysfunction following cystourethropexy: Its evaluation and management, J. Urology 144: 670–673 (1990).

Webster: "Female Urinary Incontinence," *Urologic Surgery*, J.B. Lippincott Company: Philadelphia, 1983, 665–679.

Winter: Peripubic urethropexy for urinary stress incontinence in women, Urology 20: 408–411 (1982).

Zimmern: A prospective evaluation of Four–Corner bladder neck suspension for Grade 11/111 Cystocele repair, Neurol. and Urodynamics 9: 231 (1990).

Zimmern: Transvaginal Closure of the Bladder Neck, Seminars in Urology 4: 30–32 (1986).

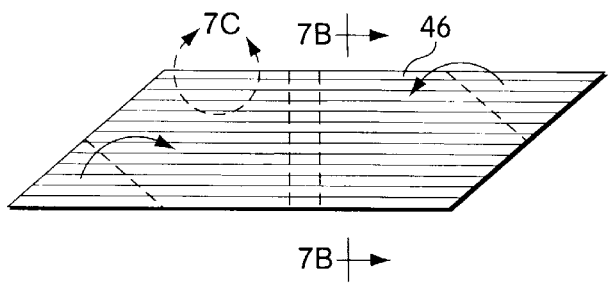
Fig. 7B
Fig. 7A
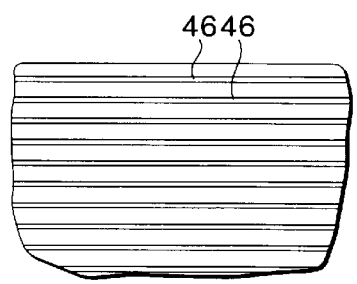
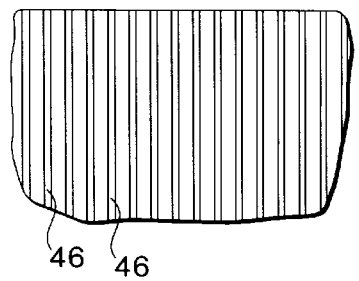
Fig. 7C
Fig. 7D
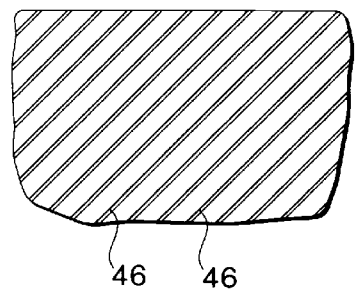
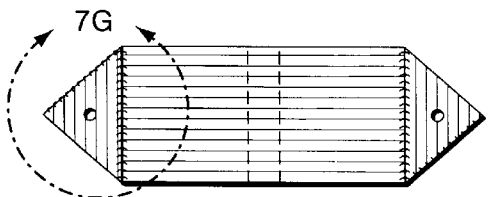
Fig. 7E
Fig. 7F
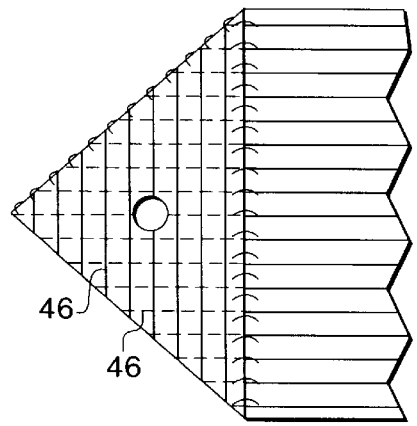
Fig. 7G

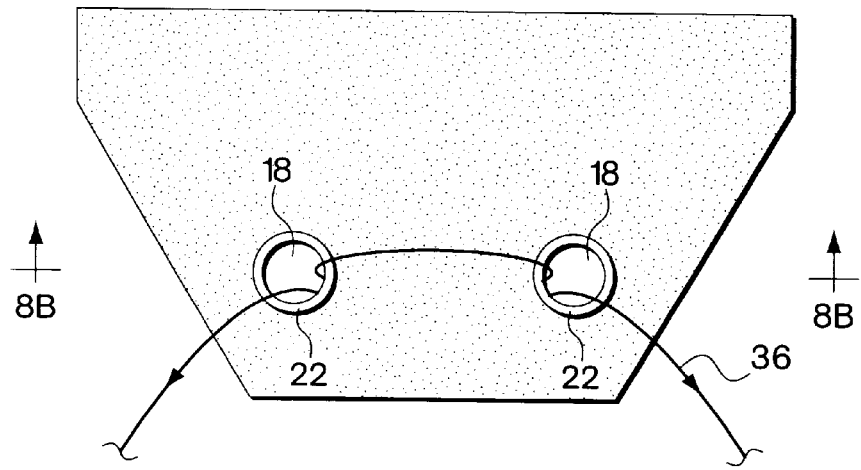
Fig. 8A
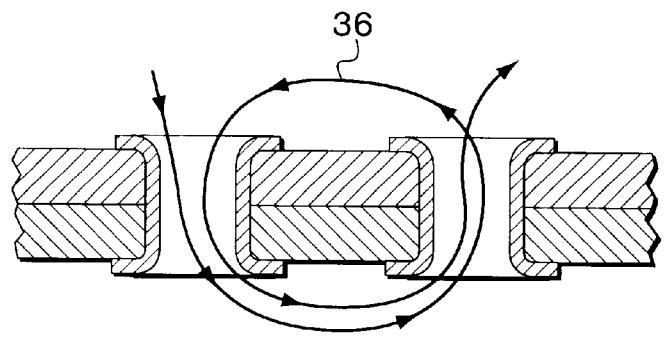
Fig. 8B
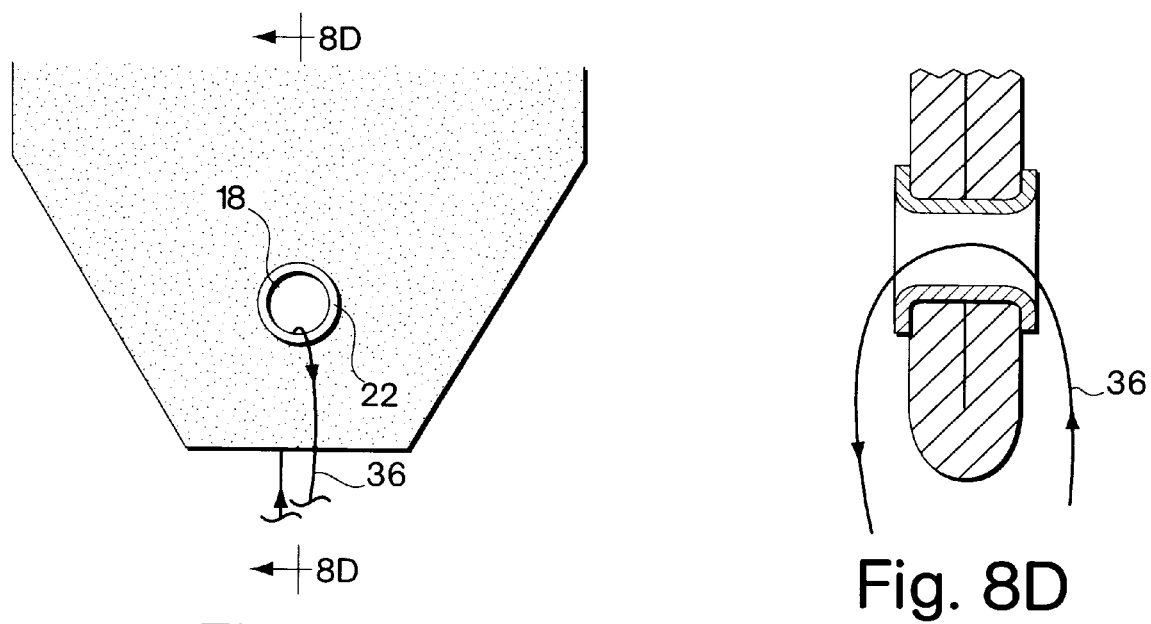
Fig. 8C
Fig. 8D

STABILIZATION SLING FOR USE IN MINIMALLY INVASIVE PELVIC SURGERY

RELATED APPLICATIONS

This application claims priority from U.S. Provisional Pat. App. Ser. No. 60/038,379 filed Feb. 13, 1997.

FIELD OF THE INVENTION

The present invention relates to slings for use in improving urinary continence. More particularly, the present invention relates to prefabricated urethral stabilization or suspension slings, methods of making the slings and kits including the slings.

BACKGROUND OF THE INVENTION

Urinary incontinence is a widespread problem in the United States and throughout the world. Urinary incontinence affects people of all ages and can severely impact a patient both physiologically and psychologically.

In approximately 30% of the women suffering from urinary incontinence, incontinence is caused by intrinsic sphincter deficiency (ISD), a condition in which the valves of the urethral sphincter do not properly coapt. In approximately another 30% of incontinent women, incontinence is caused by hypermobility, a condition in which the muscles around the bladder relax, causing the bladder neck and proximal urethra to rotate and descend in response to increases in intraabdominal pressure. Hypermobility may be the result of pregnancy or other conditions which weaken the muscles. In an additional group of women with urinary incontinence, the condition is caused by a combination of ISD and hypermobility.

In addition to the conditions described above, urinary incontinence has a number of other causes, including birth defects, disease, injury, aging, and urinary tract infection.

Numerous approaches for treating urinary incontinence are available. One such approach involves the use of a sling. At the present time, however, surgeons using a sling based procedure must grow or harvest autologous tissue or purchase processed cadaveric tissue, animal tissue, or synthetic material from a supplier and fashion the sling during the surgical procedure. Thus, during surgery, the surgeon must cut the sling to the desired dimensions and shape, and attach sutures to the sling. In addition to increasing surgical expense, these steps increase the time required for and complexity of the procedure, thereby increasing surgical morbidity and mortality.

In addition, the slings currently in use are susceptible to tearing at the sites where the sutures are attached to the sling. If the suture attachment sites tear, the sling becomes dislodged and incontinence may result. Additional surgery is required to replace the dislodged sling and restore continence.

Thus, there remains a need for a prefabricated sling which overcomes the above deficiencies. U.S. Pat. No. 5,611,515, issued Mar. 18, 1997 to Benderev et al., introduces pioneering minimally invasive percutaneous and transvaginal bladder neck stabilization approaches. The percutaneous approach of Benderev et al. involves stabilizing the bladder neck using a bone anchor which is percutaneously introduced from the abdominal side of the patient. The transvaginal approach of Benderev et al. involves stabilizing the bladder neck using a staple or bone anchor which is transvaginally placed into the pubic bone. The slings of the present invention may be used in several urethral or bladder neck stabilization procedures, including the minimally invasive percutaneous and transvaginal procedures described below and those described in Benderev et al.

SUMMARY OF THE INVENTION

The present invention relates to prefabricated urethral stabilization slings, methods of making the slings, methods of attaching sutures to the slings, kits comprising the slings, and methods of using the slings to treat urinary incontinence.

One aspect of the invention is a prefabricated sling for improving urinary continence which is made of a biocompatible material and has an elongate shape adapted for urethral stabilization. The biocompatible material has a central portion extending longitudinally between a first end portion and a second end portion and at least a pair of suture receiving sites which comprise a first site located in the first end portion of the material and a second site located in the second end portion of the material. The first site is adapted for receiving at least a first suture and the second site is adapted for receiving at least a second suture. The first site and the second site are generally disposed along a line extending longitudinally relative to the sling.

In one embodiment of the sling, the biocompatible material is directionally oriented. For example, the biocompatible directionally oriented material may be longitudinally oriented. In a further embodiment, the first and second end portions of the directionally oriented material have at least one presewn edge and are generally at least twice as thick as the central portion. In yet another embodiment, the first and second suture receiving sites have an inner diameter at least equal to the diameter of the sutures.

In a further embodiment of the sling, the biocompatible material is absorbable. In some embodiments of the sling, the biocompatible material is woven.

In yet another embodiment of the sling, the biocompatible material is coated. In some embodiments, the coating on the biocompatible material is absorbed after implantation to facilitate tissue ingrowth into the biocompatible material.

In another embodiment of the sling, the biocompatible material is impregnated with an antibiotic. In one embodiment, the sling is impregnated with bacitracin. In another embodiment, the sling is impregnated with polymixim. In another embodiment the sling is impregnated with neomycin.

In some embodiments, the sling is capable of releasing a drug. In further embodiments, the drug is released over time.

The sling may have a visual indicator for indicating the position of the sling relative to the urethra. The visual indicator may comprise at least one transversely extending line in the central portion of the material.

In some embodiments, the sling has a stabilizer for further strengthening and further reducing buckling of the sling, the stabilizer being located in the first and second end portions of the sling.

In some embodiments, the material around the periphery of the suture receiving sites is reinforced. In other embodiments, the suture receiving sites are strengthened with a reinforcing device.

Another aspect of the present invention is a prefabricated sling for improving urinary continence comprising a biocompatible material having an elongate shape adapted for urethral stabilization. In this aspect of the invention, the biocompatible material has a central portion extending longitudinally between a first end portion and a second end portion. In this aspect of the invention, the sling also has integral attachment members for suspending the sling.

Yet another aspect of the present invention is a kit for performing a urethral stabilization. The kit comprises a sterile biocompatible material having an elongate shape adapted for urethral stabilization. The biocompatible material has a central portion extending longitudinally between a first end portion and a second end portion. The biocompatible material also has at least a pair of suture receiving sites. The pair of suture receiving sites comprises a first suture receiving site located in the first end portion of the biocompatible material and a second suture receiving site located in the second end portion of the biocompatible material. The first suture receiving site is adapted for receiving at least a first suture, and the second suture receiving site is adapted for receiving at least a second suture. The first suture receiving site and the second suture receiving site are generally disposed along a line extending longitudinally relative to the sling.

In one embodiment of the kit, the sling is packaged. In another embodiment of the kit, the first and second suture receiving sites are apertures. In still another embodiment of the kit, the biocompatible material has at least a first and a second suture secured thereto. In a further embodiment of the kit, the biocompatible material is filamentous.

In still another embodiment, the filamentous material is collagen coated. In some embodiments of the kit, the sutures are looped through the apertures.

Yet another aspect of the present invention is a method of making a sling for improving urinary continence. A biocompatible material is cut into an elongate shape adapted for urethral stabilization such that the material has a central portion extending longitudinally between a first end portion and a second end portion. At least a pair of suture receiving sites is formed in the material prior to surgery. The pair of suture receiving sites comprises a first site located in the first end portion of the material and a second site located in the second end portion of the material. The first site is adapted for receiving at least a first suture and the second site is adapted for receiving at least a second suture. The first site and the second site are generally disposed along a line extending longitudinally relative to the sling. In one embodiment, the method further comprises the steps of securing at least a first suture to the first site and securing at least a second suture to the second site. In another embodiment, the method further comprises the step of sterilizing the sling. In yet another embodiment, the method further comprises the step of applying an antibiotic to the sling. In still another embodiment, the method further comprises the step of packaging the sling.

Yet another aspect of the present invention is a method of stabilizing a bladder neck to improve urinary incontinence. In one step of the method, a sling comprising a biocompatible material having an elongate shape adapted for urethral stabilization is provided. The material has a central portion extending longitudinally between a first end portion and a second end portion. The sling also comprises at least a pair of suture receiving sites. In another step of the method, a suture is secured to a bone anchor. In another step of the method, the anchor is positioned in a pubic bone. In yet another step of the method, the suture is secured to at least one of the suture receiving sites in the sling. The suture receiving sites are adapted for receiving at least one suture. The suture receiving sites comprise a first suture receiving site located in the first end portion of the material and a second suture receiving site located in the second end portion of the material. The first suture receiving site is adapted for receiving at least a first suture and the second suture receiving site is adapted for receiving at least a second suture. The first suture receiving site and the second suture receiving site are generally disposed along a line extending longitudinally relative to the sling. In another step of the method, the bladder neck is stabilized with the sling. In one embodiment, the method further comprises introducing the sling percutaneously. In another embodiment of the method, the sling is introduced without invasive surgery.

BRIEF DESCRIPTION OF THE DRAWINGS

FIG. 7A is a schematic plan view of a parallelogram shaped piece of biocompatible material having longitudinally oriented filaments, grains, striations, or polymeric chains.

FIG. 7B is a cross-sectional view of the material taken along line 7B—7B of FIG. 7A.

FIG. 7C is an enlarged view of the material taken along line 7C—7C of FIG. 7A.

FIG. 7D is an enlarged schematic view of biocompatible material having transversely oriented filaments, grains, striations, or polymeric chains.

FIG. 7E is an enlarged schematic view of biocompatible material having diagonally oriented filaments, grains, striations, or polymeric chains.

FIG. 7F is a schematic plan view of a hexagonal shaped sling obtained by folding the material of FIG. 7A as indicted by the arrows in FIG. 7A and forming apertures as suture receiving sites in the end portions of the sling.

FIG. 7G is an enlarged top view of the sling taken along line 7G—7G of FIG. 7F showing the filaments, grains, striations, or polymeric chains in an upper layer of an end portion of the sling crossing the filaments, grains, striations, or polymeric chains in the underlying layer.

FIG. 8A is an enlarged top view of an end portion of a sling having a suture looped through a plurality of suture receiving sites.

FIG. 8B is a cross-sectional view of the sling taken along line 8B—8B of FIG. 8A.

FIG. 8C is an enlarged top view of an end portion of a sling having a suture threaded through a suture receiving site.

FIG. 8D is a cross-sectional view of the sling taken along line 8D—8D of FIG. 8C.

DETAILED DESCRIPTION OF THE PREFERRED EMBODIMENTS

The present invention relates to prefabricated slings for use in urethral floor reconstruction. More particularly, the slings are useful for improving or maintaining urinary continence such as by suspending, stabilizing and/or slightly compressing the urethra of an incontinent patient. The slings are particularly useful for treating patients suffering from incontinence caused by Intrinsic Sphincter Deficiency (ISD) and/or hypermobility. The slings may also be used to treat other disorders in which stabilization and/or compression of the urethra would be beneficial.

The present slings are designed to be implanted in a patient suffering from incontinence using the medical procedure described in more detail below. During implantation, the sling is preferably positioned beneath the bladder neck so that the urethra extends across the center of the sling. The sling is biased towards the urethra through tension applied to the sling by sutures or other attachment means, which are preferably anchored to the pubic bone. The resulting bias stabilizes and/or slightly compresses the urethra so that continence is maintained.

Although urethral slings have previously been used to treat incontinence, the present slings are prefabricated, eliminating the need for the surgeon to prepare them for use during the surgical procedure. The present slings are supplied to the physician in shapes and dimensions adapted for urethral stabilization or suspension, eliminating the need for the surgeon to cut the sling material during surgery. In addition, the present slings are provided with suture receiving sites already prepared so that the surgeon need not manufacture them during surgery. The slings may also be provided with reinforced suture receiving sites to reduce the incidence of tearing about the point of suture attachment. Because the surgeon need not fabricate the sling during surgery, the time required for the surgical procedure is reduced.

In some embodiments, the slings are provided with the sutures preattached. Alternatively, the slings may have preformed integral attachment members which, like the sutures, allow the sling to be suspended from structures such as the pubic bone. In either case, the need for the surgeon to attach sutures to the sling during surgery is eliminated, thereby simplifying the implantation procedure.

The foregoing features of the present invention overcome the above-discussed deficiencies of slings currently in use. By simplifying and shortening the surgical procedure, use of the slings of the present invention results in decreased surgical morbidity and mortality.

Figure 1:
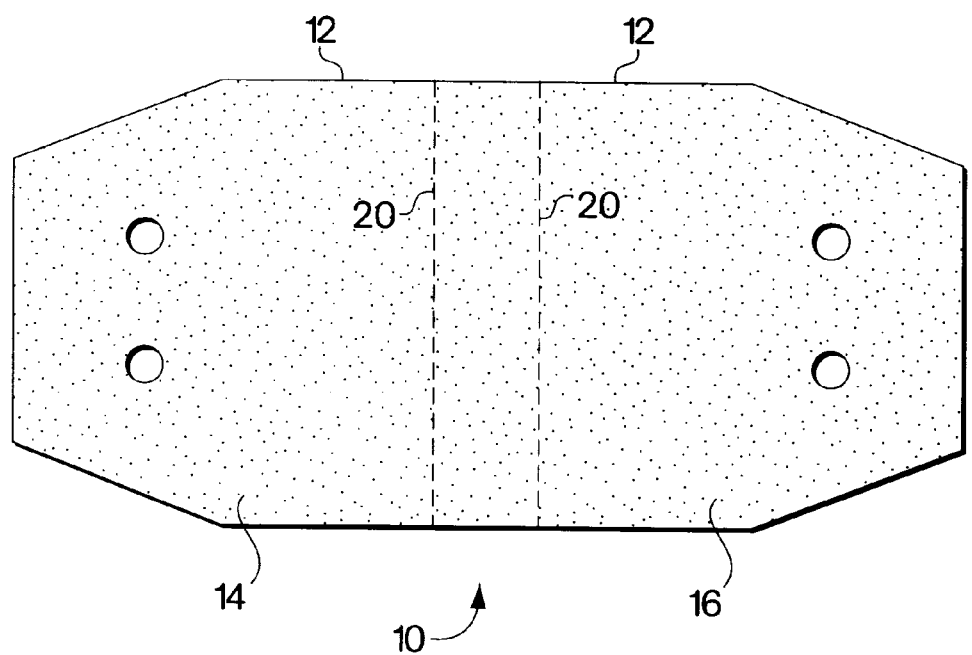
FIG. 1 is a plan view of a preferred embodiment of the sling of the present invention.

Referring to FIG. 1, there is disclosed a plan view of a preferred embodiment of the sling 10 of the present invention. The sling of FIG. 1 has been cut into a generally elongate shape adapted for urethral stabilization, with a central portion 12 extending between a first end portion 14 and a second end portion 16. Suture receiving sites 18 are prefabricated in the first and second end portions 14, 16 of the sling 10. The sling preferably also has a visual indicator 20. These and other features of the present invention will be described in more detail below after discussing the materials from which the sling can be constructed.

The sling may be fabricated from any of a variety of synthetic or naturally occurring biocompatible materials. Such materials may be filamentous or non-filamentous, elastic or inelastic, and may be porous, microporous, perforated, or impermeable. The properties of the sling may be selected as appropriate based on the surgical procedure used to implant the sling and the application for which the sling is used.

Filamentous materials suitable for use in the slings of the present invention include cadaveric or animal tissue such as fascia lata, rectus fascia or processed collagen. Synthetic materials such as polyester, polyurethane, or nylon can also be used. The synthetic filamentous material can be woven or non-woven. Filaments made from synthetic materials may be braided together to form strands or threads which can be braided or woven together to form strips of fabric. Preferably, the synthetic filamentous material is polyester.

Non-filamentous materials suitable for use in the slings of the present invention include silicone, polytetrafluoroethylene (PTFE), polyethylene terephthalate (PET), FEP (fluorinated ethylene propylene), or thin films such as latex.

As will be apparent to one skilled in the art, the elasticity of the sling material may also be selected based on the type of surgical procedure for which the sling is being used. A suitable elastic material is knitted polyester.

As will be apparent to one skilled in the art, inelastic or minimally elastic materials may be preferred for certain procedures such as those in which the sling is used to create an immobile floor. A preferred minimally elastic material is woven polyester.

The porosity of the material may also be selected based on the type of surgical procedure for which the sling is being used. For example, pores, micropores, or perforations permit tissue ingrowth, which is advantageous to stabilize the sling and reduce erosion from constant motion.

Additionally, the sling material may be impregnated with antibiotics or other agents which can be delivered from the surface of the sling as well as through the pores, micropores or perforations. Impregnation with antibiotics or other agents may be facilitated by coating the sling with collagen.

Impermeable materials may also be useful in certain applications of the sling. Representative impermeable materials include nylons and polyester. A preferred impermeable material is polyester.

A coating may also be applied to the sling. The coating may be used to deliver a number of compounds, such as antibiotics, heparin, immunosuppressant agents or other drugs. In some embodiments, the drug may be released over time. The coating also blocks the interstices of the underlying sling material, thereby decreasing the risk of infection by sequestering the interstices of the sling from contact with microorganisms encountered during implantation of the sling. Preferably, the coating is absorbed after implantation to facilitate tissue ingrowth into the interstices, pores, micropores and/or perforations of the sling material.

Suitable coatings include polyglycolic acid, polylactic acid, blends of polyglycolic acid and polylactic acid, gelatin, polyvinyl alcohol, and polyvinyl pyrrolidone. A preferred coating is a smooth layer of collagen, such as that provided on the Hemashield® woven double velour available from Meadox. (Meadox Medical, 112 Beaver Drive, Oakland, N.J. 07436 or Boston Scientific Corporation, One Boston Scientific Place, Natick, Mass. 01760.) The smooth collagen coating protects the interstices of the underlying sling material from bacterial contact during implantation, thereby decreasing the risk of infection as previously discussed. Additionally, the collagen coating facilitates the uptake of antibiotics to reduce the risk of infection as discussed below. After placement in the body, the collagen is gradually absorbed, facilitating tissue ingrowth into the underlying filamentous mesh. The collagen coating may also enhance tissue compatibility.

The slings of the present invention may also be made of absorbable materials. Such absorbable slings preferably remain structurally intact for at least three months while supporting tissue ingrowth. Thereafter, the slings may be fully absorbed. Preferably, the slings are fully absorbed over a period of 3–6 months following the three month period in which the sling is intact. Preferably, the absorbable sling is made of polylactic acid or polylactic acid/polyglycolic acid copolymers.

The slings of the present invention may be fabricated from directionally oriented biocompatible materials. Such materials include filamentous materials in which the orientation of the filaments is directionally ordered, as well as grained or striated materials in which the grains or striations are directionally ordered. Alternatively, the material may be a polymeric material in which the orientation of the polymeric chains comprising the material is directionally ordered. The polymeric material may or may not be cross-linked.

The filaments, grains, striations, or polymeric chains in such materials may be oriented in a single direction or may be multidirectional. Suitable directionally oriented materials include synthetic materials such as Trelex® Natural Mesh (Meadox Medical, 112 Beaver Drive, Oakland, N.J. 07436 or Boston Scientific Corporation, One Boston Scientific Place, Natick, Mass. 01760.), Hemashield®, and woven and knitted polyester.

Alternatively, the directionally oriented material may be natural material such as grained or striated tissue. The tissue may be an allograft, xenograft, or autologous tissue. One advantage of autologous tissue is its ability to revascularize and regrow after implantation.

Tissue for use in allografts can be obtained from cadavers. Cadaveric tissue can be harvested according to techniques well known to those skilled in the art and may be selected to minimize the risk of rejection. However, non-cadaveric tissue is generally preferred because of patient preference and the perceived risk of cross-contamination. Although the cadaveric tissue may be absorbed after implantation, the scar tissue which replaces the cadaveric tissue provides support for the bladder neck.

Representative sources of autologous tissue for use in the present slings include striated muscle, fascia lata, rectus fascia, dura, pericardium and the vaginal wall. The same tissue sources may also be used for allografts. Typical sources of xenograft tissue include striated muscle, bovine fascia, dura, pericardium and collagen.

In addition to the synthetic and naturally occurring biocompatible materials enumerated above, those skilled in the art will appreciate that a variety of other materials may be readily employed in the slings of the present invention.

Figure 2A:
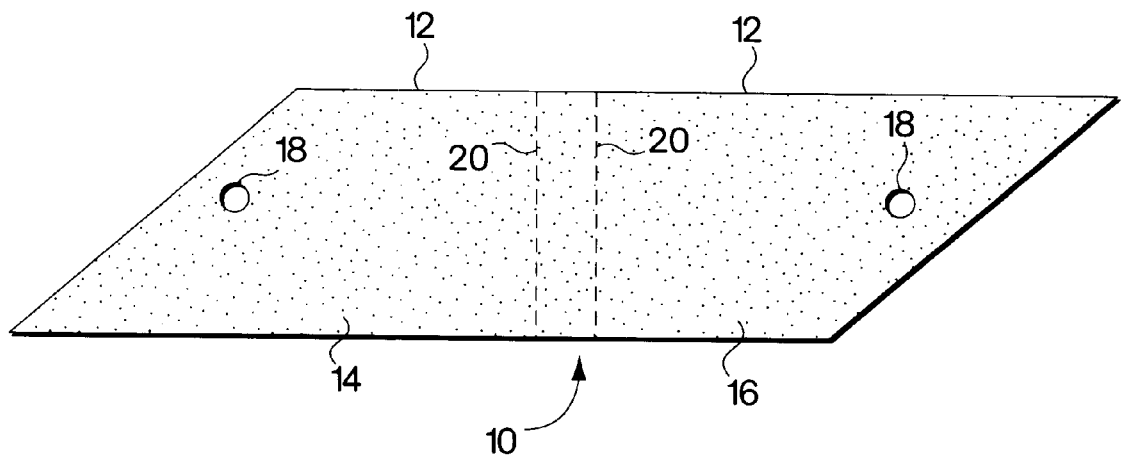
FIG. 2A is a plan view of a parallelogram shaped embodiment of the sling of the present invention.
Figure 2B:
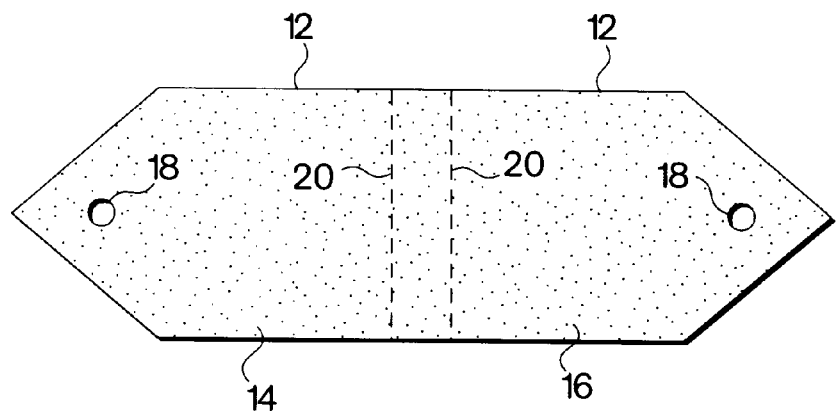
FIG. 2B is a plan view of a hexagonal shaped embodiment of the sling of the present invention.
Figure 2C:
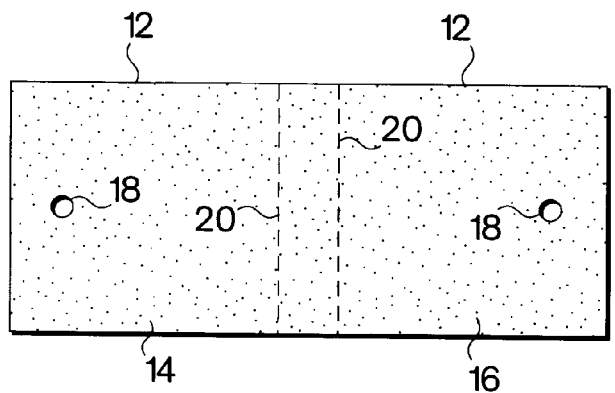
FIG. 2C is a plan view of a rectangular shaped embodiment of the sling of the present invention.

In addition to the elongate octagonal sling illustrated in FIG. 1, the slings of the present invention may be cut into a number of other shapes. For example, several alternative elongate shapes suitable for use in the present invention are shown in FIGS. 2A–2C. These include parallelograms such as rhomboids (FIG. 2A), hexagons (FIG. 2B), and rectangles (FIG. 2C). In addition, the end portion of the sling may be cut into a rounded shape, such as that illustrated in FIG. 4B. The optimal shape of the sling is related to anatomical considerations as well as the surgical procedure used to introduce the sling. For instance, slings having rounded ends (FIG. 4B) or tapered ends, such as the hexagon (FIG. 2B), parallelogram (FIG. 2A), and octagon (FIG. 1), may facilitate insertion into the pocket formed during the surgical procedure discussed in more detail below, since the pocket may not be precisely rectangular.

The optimal dimensions of the sling can be varied considerably to suit particular design criteria desired for a particular application and still embody the present invention. For example, optimal sling dimensions are dependent upon anatomical considerations and the surgical procedure used to introduce and attach the sling. For instance, the optimal length of the sling may be influenced by whether the surgeon prefers to attach a long strip of material to the pubic bone or abdominal musculature with a bone anchor or other securing device. In such procedures, the sling may be up to 30 cm in length and may be 1–5 cm in width. Preferably, the long slings used in such procedures are 15–30 cm in length and 3–5 cm in width. Shorter slings may be preferred for procedures in which the sling is suspended by a suture bridge. Such slings may be 2.5–7 cm in length and 1–5 cm in width.

The optimal dimensions of the sling may also be influenced by the sling material selected. For instance, the thickness of the sling material may be dependent on the material selected and the strength and tear resistance required for a particular application of the sling.

Figure 3A:
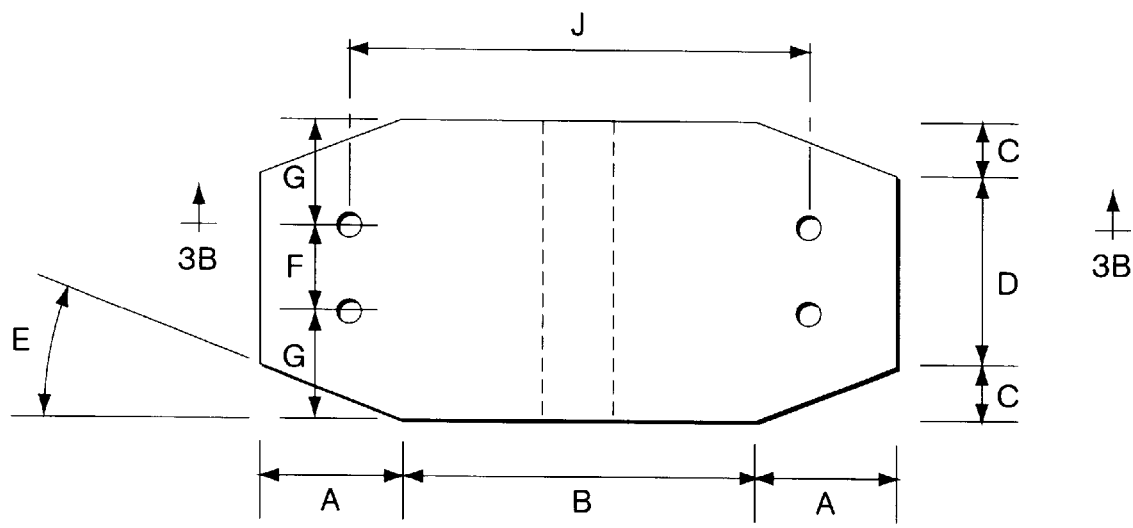
FIG. 3A is a plan view of a preferred embodiment of the sling of the present invention showing preferred dimensions.
Figure 3B:
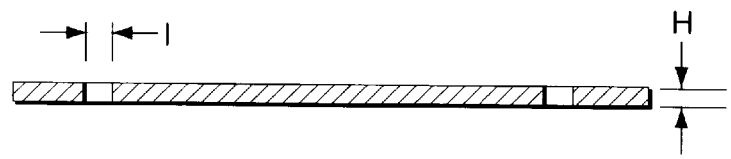
FIG. 3B is a cross-sectional view of the sling taken along line 3B—3B of FIG. 3A.

The dimensions of the preferred embodiment of FIG. 1 are shown in FIGS. 3A and 3B. The approximate dimensions, in inches, are as follows: A=0.30; B=0.79; C=0.12; D=0.43; F=0.20; G=0.24; H=0.015; I=0.030; and J=0.98. Angle E=22°.

As indicated above, the sling 10 is preferably provided with a visual indicator 20. The visual indicator enables the surgeon to position the sling relative to the urethra so that the urethra generally extends across the center of the sling. In one embodiment, the visual indicator 20 comprises two transversely extending dashed lines in the central portion 12 of the sling 10 as illustrated in FIG. 1. However, those skilled in the art will recognize that a variety of other types of visual indicators, including radiopaque indicators, could be used in accordance with the present invention.

The sling of the present invention preferably also has at least one suture receiving site formed in both the first and second end portions of the sling. Preferably, the suture receiving site is an aperture. The aperture may be formed by die stamping ultrasonic cutting, heat cauterizing the sling material, or piercing the sling material with a hot poker. Alternatively, the suture receiving site may be sling material as discussed below in regard to FIGS. 5I and 5J.

The suture receiving site is adapted for receiving at least one suture. Preferably, the suture receiving site has an inner diameter at least equal to the diameter of the suture to be received therein. In the preferred embodiment depicted in FIG. 1, both the first and second end portions of the sling have two apertures which are equally displaced from the central longitudinal axis of the sling. However, numerous alternative embodiments are also contemplated by the present invention.

Figure 4A:
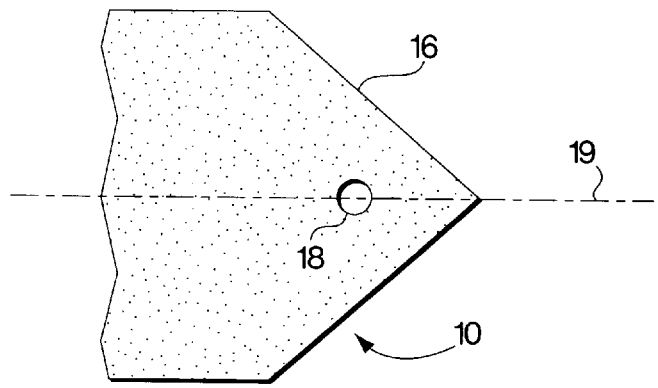
FIG. 4A is a partial top view of an end portion of a sling having a single suture receiving site.

For example, some embodiments of the sling, such as that depicted in FIG. 4A, have only one suture receiving site formed per end portion. In such embodiments, the suture receiving site 18 is preferably located along the central longitudinal axis 19 of the sling.

Other embodiments of the sling have 3 or more suture receiving sites formed per end portion. In such embodiments, preferably at least one suture receiving site 18 is located along the central longitudinal axis 19 of the sling with the other suture receiving sites 18 being located symmetrically about the central longitudinal axis 19 as illustrated in FIG. 4C.

Figure 4B:
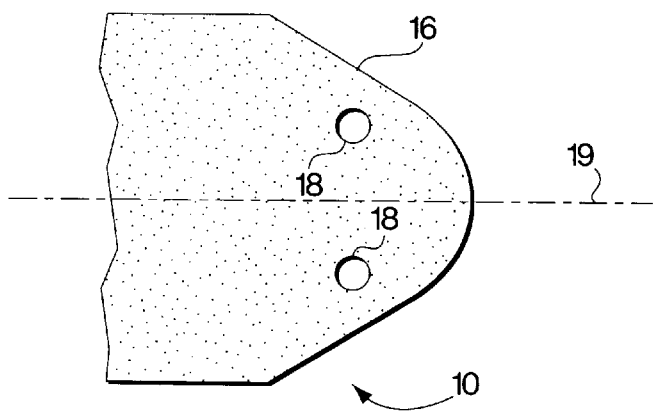
FIG. 4B is a partial top view of a rounded end portion of a sling having two suture receiving sites.
Figure 4C:
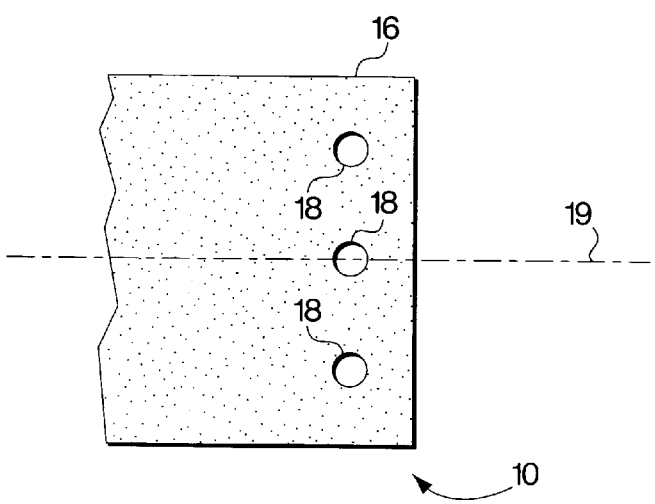
FIG. 4C is a partial top view of an end portion of a sling having three suture receiving sites.

Preferably, in embodiments in which the number of suture receiving sites in each end portion of the sling is odd, at least one suture receiving site in each end portion of the sling is located along the central longitudinal axis of the sling as shown in FIGS. 4A and 4C. In those embodiments in which the number of suture receiving sites in each end portion of the sling is even, the suture receiving sites are preferably disposed symmetrically about the central longitudinal axis of the sling as depicted in FIGS. 1 and 4B.

The use of a plurality of suture receiving sites in each end portion of the sling results in reduced buckling of the sling after implantation compared to embodiments having a single suture receiving site at each end of the sling. Thus, embodiments having a plurality of suture receiving sites in each end portion are preferred.

Although several examples of the locations and number of the suture receiving sites in the end portions of the present slings have been provided above, those skilled in the art will appreciate that additional configurations fall within the scope of the present invention. It will also be appreciated by those skilled in the art that the various configurations and numbers of suture receiving sites described above may be utilized with any of the sling shapes or biocompatible materials described above.

FIG. 5 shows various types of suture receiving sites which may be used in the slings of the present invention. In FIGS. 5A and 5B, the suture receiving site is an aperture formed in the sling material. This type of suture receiving site is employed in the embodiment shown in FIG. 1. Preferably, the material around the periphery of the suture receiving sites is reinforced by heat sealing or ultrasonic sealing.

Figure 5A:
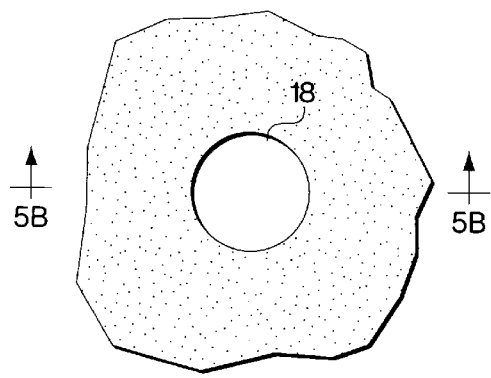
FIG. 5A is an enlarged top view of an end portion of a sling in which the suture receiving site is an aperture.
Figure 5C:
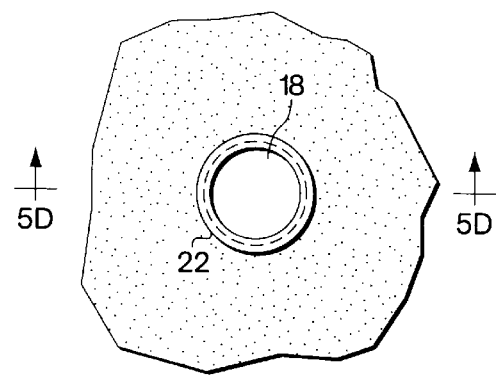
FIG. 5C is an enlarged top view of an end portion of a sling having a reinforcing device in the suture receiving site.
Figure 5B:
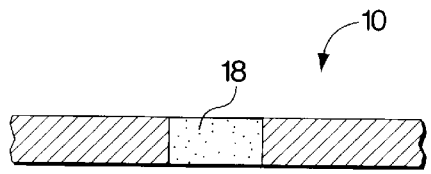
FIG. 5B is a cross-sectional view of the end portion taken along line 5B—5B of FIG. 5A.
Figure 5D:
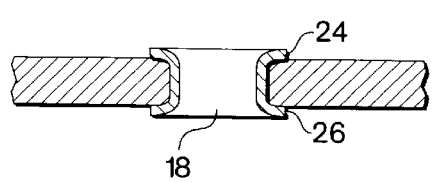
FIG. 5D is a cross-sectional view of the end portion taken along line 5D—5D of FIG. 5C.

In addition, the suture receiving sites can be strengthened in order to minimize the possibility of tearing. For instance, one piece reinforcing devices may be inserted in the apertures in the sling material. As shown in FIGS. 5C and 5D, the one piece reinforcing device 22 has an upper rim 24 and a lower rim 26 between which the sling material bordering the suture receiving site is enclosed. Although the upper rim and the lower rim are shown parallel to one another in FIG. 5D, alternative embodiments are contemplated in which the upper and lower rims converge towards each other with the sling material therebetween. The upper rim and the lower rim may also be provided with friction enhancing retention structures to minimize the risk of dislodgement of the one piece reinforcing device. Preferably, the one piece reinforcing device 22 is fabricated from biocompatible plastics or metals, such as stainless steel or titanium.

Figure 5E:
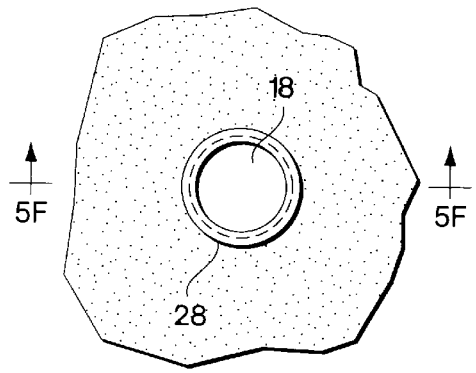
FIG. 5E is an enlarged top view of an end portion of a sling having an alternative reinforcing device in the suture receiving site.
Figure 5G:
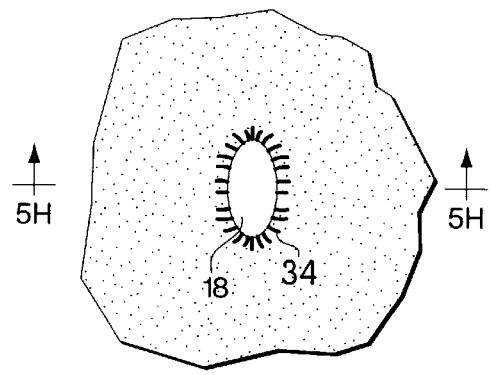
FIG. 5G is an enlarged top view of an end portion of a sling having reinforced material around the periphery of the suture receiving site.
Figure 5F:
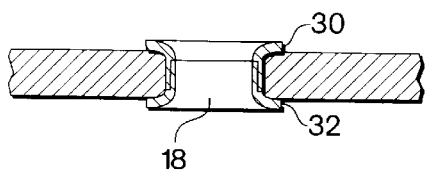
FIG. 5F is a cross-sectional view of the end portion taken along line 5F—5F of FIG. 5E.

Alternatively, the area around an aperture 18 in the sling material may be strengthened by inserting a multiple piece reinforcing device 28 therein. As illustrated in FIGS. 5E and 5F, the multiple piece reinforcing device 28 has a first piece 30 and a second piece 32, which interlock and enclose the sling material bordering the suture receiving site. Although the first piece and the second piece are shown parallel to one another in FIG. 5F, alternative embodiments are contemplated in which they converge towards each other as discussed above with respect to the one piece reinforcing device. The first piece and the second piece may also be provided with friction enhancing retention structures to minimize the risk of dislodgement of the multiple piece reinforcing device. Preferably, the multiple piece reinforcing device 28 is fabricated from biocompatible plastics or metals, such as stainless steel or titanium.

Figure 5H:
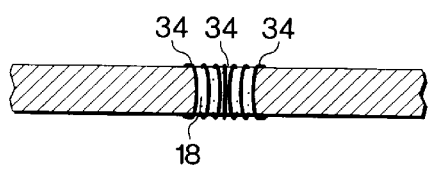
FIG. 5H is a cross-sectional view of the end portion taken along line 5H—5H of FIG. 5G.
Figure 5I:
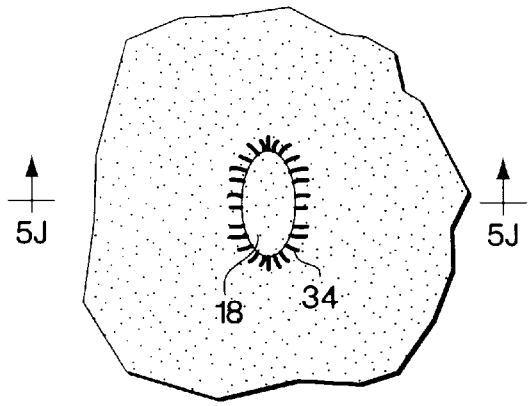
FIG. 5I is an enlarged top view of an end portion of a sling having reinforced material around an alternative suture receiving site.
Figure 5J:
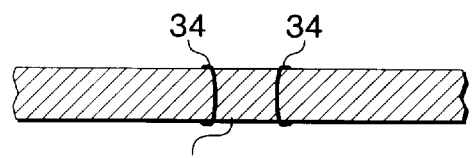
FIG. 5J is a cross-sectional view of the end portion taken along line 5J—5J of FIG. 5I.
Figure 5K:
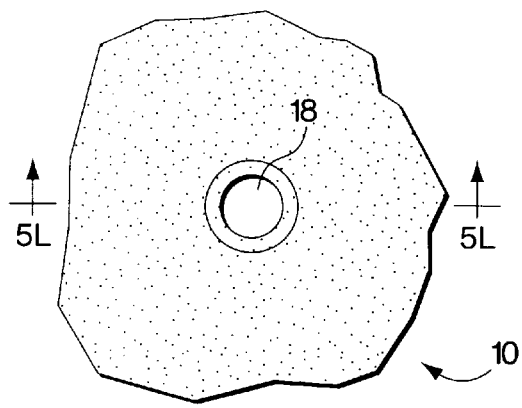
FIG. 5K is an enlarged top view of an end portion of a sling in which the suture receiving site is an aperture and the material around the periphery of the suture receiving site has been reinforced by heat sealing or ultrasonically sealing.
Figure 5L:
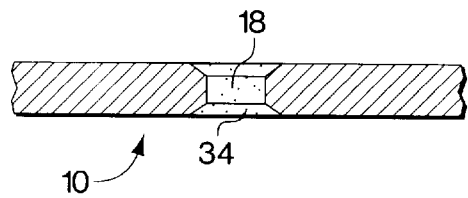
FIG. 5L is a cross-sectional view of the end portion taken along line 5L—5L of FIG. 5K.

Yet another way of reducing the risk of tearing comprises reinforcing the sling material around the periphery of the suture receiving sites. Slings having such reinforced material around the periphery of the suture receiving site are depicted schematically in FIGS. 5G through 5J. In FIGS. 5G and 5H, the suture receiving site is an aperture. In FIGS. 5I and 5J, the suture receiving site comprises sling material. In the embodiment of FIGS. 5I and 5J, the sling material at the suture receiving site provides a puncture target into which the surgeon can insert the suspending suture. In FIGS. 5K and 5L the suture receiving site is an aperture and the periphery of the suture receiving site is reinforced by heat sealing or ultrasonically sealing. Preferably, the material around the periphery of the suture receiving sites is reinforced by heat sealing or ultrasonic sealing. The reinforced material 34 around the periphery of the suture receiving site shown in FIGS. 5G through 5L may be formed in a variety of ways, such as by heat sealing, ultrasonically sealing, or sewing the area of the sling material along the periphery of the suture receiving site.

Figure 6A:
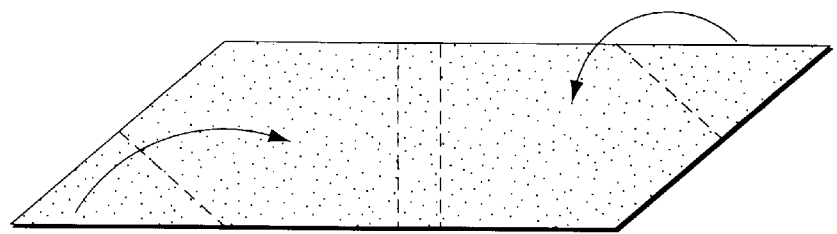
FIG. 6A is a plan view of an unfolded parallelogram shaped piece of biocompatible material.
Figure 6B:
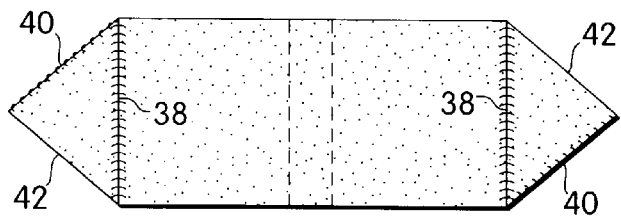
FIG. 6B is a plan view of a hexagonal shaped piece of material obtained by folding the material of FIG. 6A as indicated by the arrows in FIG. 6A.
Figure 6C:
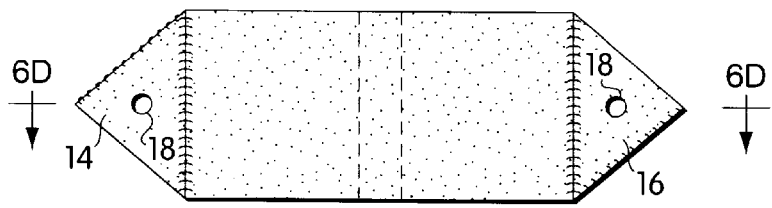
FIG. 6C is a plan view of a hexagonal shaped sling in which apertures have been formed as suture receiving sites in the end portions of the sling.
Figure 6D:
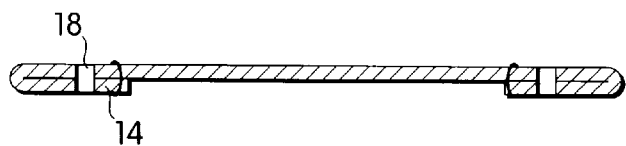
FIG. 6D is a cross-sectional view of the hexagonal shaped sling taken along line 6D—6D of FIG. 6C.
Figure 6E:
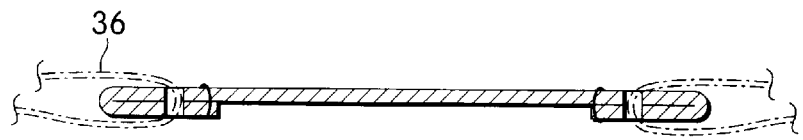
FIG. 6E is the cross-sectional view of FIG. 6D showing sutures secured to the apertures of the sling.
Figure 6F:
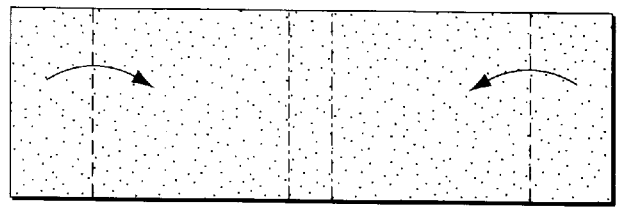
FIG. 6F is a plan view of an unfolded rectangular shaped piece of biocompatible material.
Figure 6G:
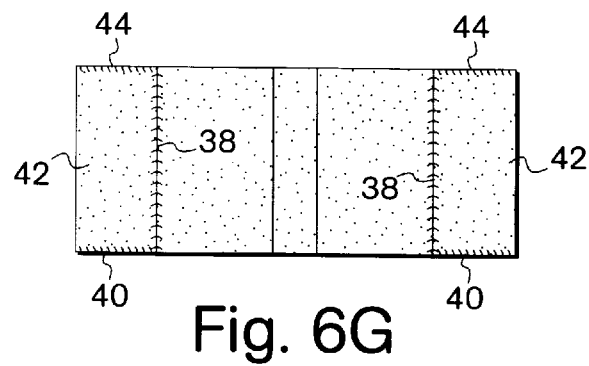
FIG. 6G is a plan view of a rectangular shaped piece of material obtained by folding the material of FIG. 6F as indicated by the arrows in FIG. 6F.
Figure 6H:
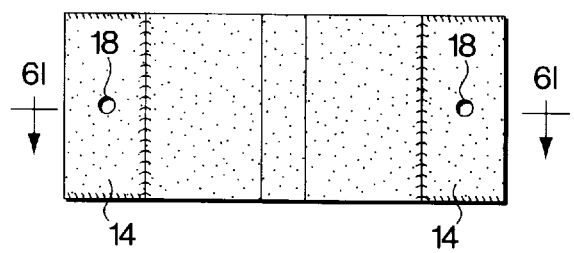
FIG. 6H is a plan view of a rectangular sling in which apertures have been formed as suture receiving sites in the end portions of the sling.
Figure 6I:
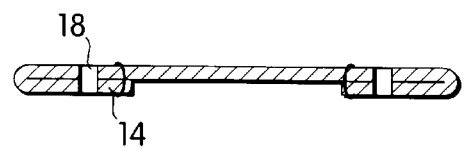
FIG. 6I is a cross-sectional view of the rectangular shaped sling taken along line 6I—6I of FIG. 6H.
Figure 6J:
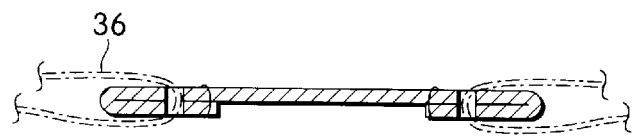
FIG. 6J is the cross-sectional view of FIG. 6I showing sutures secured to the apertures of the sling.
Figure 6K:
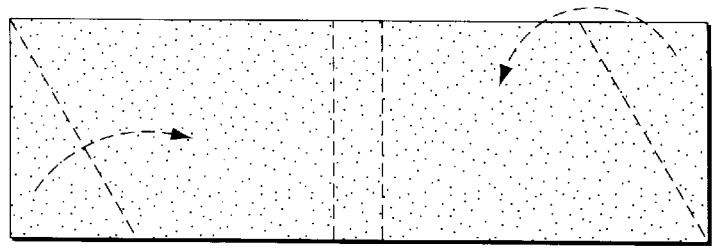
FIG. 6K is a plan view of an unfolded rectangular piece of biocompatible material.
Figure 6L:
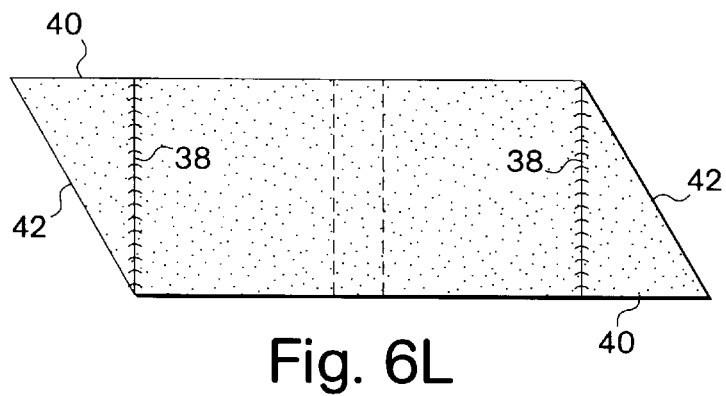
FIG. 6L is a plan view of a parallelogram shaped piece of material obtained by folding the material of FIG. 6K as indicated by the arrows in FIG. 6K.
Figure 6M:
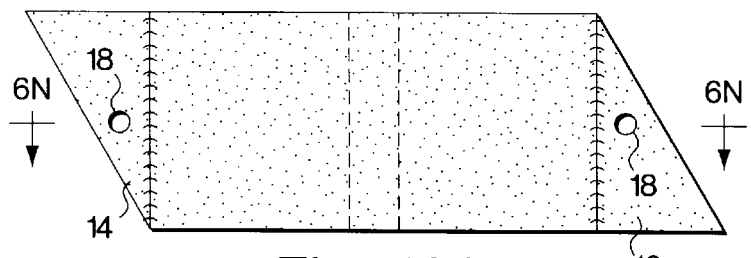
FIG. 6M is a plan view of a parallelogram shaped sling in which apertures have been formed as suture receiving sites in the end portions of the sling.
Figure 6N:
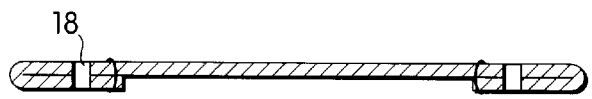
FIG. 6N is a cross-sectional view of the parallelogram shaped sling taken along line 6N—6N of FIG. 6M.
Figure 6O:
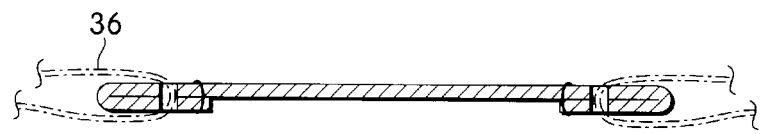
FIG. 6O is the cross-sectional view of FIG. 6N showing sutures secured to the apertures of the sling.

In further embodiments of the present invention, the periphery of the suture receiving sites is strengthened by making the end portions of the sling thicker than the central portion as shown in FIGS. 6A–6O. One way to fabricate slings in which the end portions are thicker than the central portion is to fold the end portions of the sling. For example, a hexagonal shaped piece of material, shown in FIG. 6B, may be formed by folding the parallelogram shaped piece of biocompatible material shown in FIG. 6A along the lines indicated in FIG. 6A. Alternatively, the hexagonal material of FIG. 6B may be formed by folding a trapezoidal piece of material, as will be apparent to one skilled in the art. Suture receiving sites may be formed in the hexagonal shaped intermediate of FIG. 6B to form the hexagonal shaped sling of FIG. 6C, in which the end portions 14, 16 are generally twice the thickness of the central portion 12 of the sling. A cross-sectional view of the hexagonal shaped sling depicting the double thickness end portions is shown in FIG. 6D. FIG. 6E illustrates a suture 36 secured in the suture receiving site 18. The suture can be secured to the suture receiving site during the manufacturing process of the sling or by the physician prior to or during surgery.

In another embodiment, a rectangular piece of material, shown in FIG. 6G, may be formed by folding the rectangular piece of biocompatible material shown in FIG. 6F along the lines indicated in FIG. 6F. Suture receiving sites may be formed in the rectangular shaped intermediate of FIG. 6G to form the rectangular sling of FIG. 6H, in which the end portions 14, 16 are generally twice the thickness of the central portion 12 of the sling. A cross-sectional view of the rectangular shaped sling depicting the double thickness end portions is shown in FIG. 6I. FIG. 6J illustrates a suture 36 secured in the suture receiving site 18 as discussed above with regard to FIG. 6E.

In a further embodiment, a rhomboid shaped piece of material, shown in FIG. 6L, may be formed by folding the rectangular piece of biocompatible material shown in FIG. 6K along the lines indicated in FIG. 6K. Suture receiving sites may be formed in the rhomboid shaped intermediate of FIG. 6L to form the rhomboid shaped sling of FIG. 6M, in which the end portions 14, 16 are generally twice the thickness of the central portion 12 of the sling. A cross-sectional view of the rhomboid shaped sling depicting the double thickness end portions is shown in FIG. 6N. FIG. 6O illustrates a suture 36 secured in the suture receiving site 18 as discussed above with regard to FIGS. 6E and 6J.

Those skilled in the art will appreciate that slings in which the end portions are thicker than the central portion may be made in any of the shapes and configurations disclosed herein and are not limited to the shapes illustrated in FIGS. 6A–6O.

In some embodiments of the present invention, at least one edge 38, 40, 42 or 44 of each double thickness end portion 14, 16 is secured to an adjacent layer of the sling either during manufacturing of the sling or by the physician prior to or during the surgical procedure. Alternatively, the sling may be supplied to the surgeon with at least one edge 38, 40, 42 or 44 of each double thickness end portion 14, 16 already secured. Preferably, the edge 38 closest to the central portion 12 is sewn. More preferably, all edges 38, 40, 42 and 44 are secured. In those embodiments in which the sling is made from natural tissue, the edge 42 where the fold was made is preferably not secured, although the other edges 38, 40 and/or 44 of the double thickness end portions may be secured. Numerous methods familiar to those skilled in the art may be used to secure the edges, such as sewing, heat sealing, ultrasonic sealing, stapling or gluing. Preferably, the edges are secured by sewing during the manufacturing process or prior to surgery, and by sewing, stapling or gluing during the surgical procedure.

As will be apparent to one of skill in the art, slings having end portions that are thicker than the central portion can be made in a variety of ways other than those described above. For example, the sling material may be folded over on itself more than once to produce slings with end portions more than twice as thick as the central portion. Alternatively, an additional layer or layers of separately cut material could be secured to the end portions of the sling, thereby producing a sling having end portions of varying thickness. Slings having two or more layers of material in both the end portions and the central portion are also contemplated. Such slings can be formed by securing the upper layer or layers of sling material to the lower layer or layers using the methods discussed above.

In addition to the resistance to tearing provided by slings in which the suture receiving sites are located in end portions that are thicker than the central portion, a further benefit is provided by securing the upper layer of the vertical edge 38 to the lower layer of the sling. In particular, the secured vertical edge 38 acts as a reinforcing rib which reduces buckling of the sling when the sling is placed under tension after implantation in the patient.

If the suture receiving sites are strengthened using the one piece reinforcement devices, two piece reinforcement devices, or reinforced material around their periphery as described above, the edges 40, 42, 44 of the double thickness end portions of the sling may be secured. The vertical edge 38, however, may be secured to reduce buckling as described above.

Yet a further advantage is provided by forming end portions having double thickness in slings made of directionally oriented materials such as the materials shown in FIGS. 7A–7G. The directionally ordered filaments, grains, striations or polymeric chains may be oriented in a variety of directions. For example, FIGS. 7C–7E illustrate enlarged views of sling materials having longitudinally (FIG. 7C), transversely (FIG. 7D), and diagonally (FIG. 7E) oriented filaments, grains, striations or polymeric chains 46, all of which are suitable for use in the present invention. FIG. 7B is a schematic view of grained materials suitable for use with the present invention. Those skilled in the art will appreciate that the grained materials may have ridges or grooves therein, or may have a smooth surface. Materials having multidirectional filaments, grains, striations or polymeric chains are also suitable for use in the present invention.

The parallelogram or rhomboid shaped material of FIG. 7A can be folded along the indicated lines to form the hexagonal shaped sling having double thickness end portions shown in FIG. 7F as described above with regard to FIGS. 6A–6E. As can be seen in FIGS. 7F and 7G, when the directionally oriented material is folded over on itself, the filaments, grains, striations or polymeric chains in the upper layer of the double thickness end portion cross the filaments, grains, striations or polymeric chains in the lower layer of the end portion. This nonparallel orientation of the layers of the material relative to each other provides additional protection against tearing in the regions of the sling surrounding the suture receiving sites by having the strength of the grain perpendicular to the suture pull direction.

Slings having two or more layers of directionally oriented material in both the end portions and the central portion, wherein the filaments, grains, striations or polymeric chains in the different layers cross are also contemplated.

In another embodiment, the slings may have a stabilizer attached to the end portions 14, 16 to reduce buckling of the sling 10 and to provide additional strength to the sling 10, as depicted in FIGS. 9A–9D. Preferably, the stabilizer is made of metal or plastic. The stabilizer may be attached to the sling in a variety of manners such as sewing, heat sealing, mechanical securement, or capturing the stabilizer between a fold in the sling material. In some embodiments, the stabilizer may also be provided with friction enhancing retention structures to minimize the risk of dislodgement of the stabilizer.

Figure 9A:
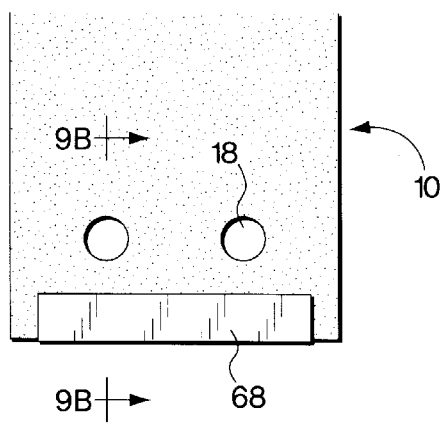
FIG. 9A is a plan view of an end portion of a sling having a stabilizer attached thereto.
Figure 9B:
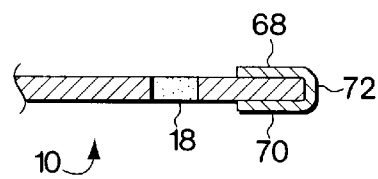
FIG. 9B is a cross-sectional view of the sling taken along line 9B—9B of FIG. 9A.

In one embodiment, the stabilizer may be attached to an edge at each end of the sling as illustrated in FIGS. 9A and 9B. The stabilizer may comprise a first side 68, a second side 70, and an intermediate section 72 disposed between the first side 68 and the second side 70. In this embodiment, the stabilizer preferably contacts both sides of the sling 10.

Figure 9C:
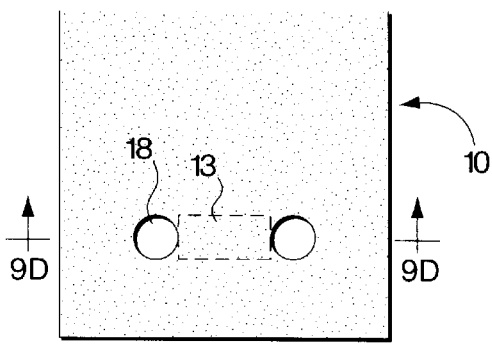
FIG. 9C is a plan view of an end portion of a sling having a stabilizer between the suture receiving sites.
Figure 9D:
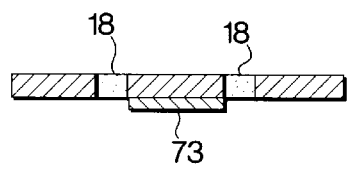
FIG. 9D is a cross-sectional view of the sling taken along line 9D—9D of FIG. 9C.

In an alternate embodiment, the stabilizer may comprise a single section 73 which is disposed between the suture receiving sites 18 and is attached to one side of the sling as illustrated in FIGS. 9C and 9D.

Those skilled in the art will appreciate that additional stabilizer designs and locations are possible. For example, a stabilizer which is located at each end of the sling may contact a single side of the sling 10. In other embodiments, the sling may have one or more stabilizers in the central portion 12 in addition to the stabilizers in the end portions 14, 16. In addition, those skilled in the art will appreciate that the stabilizers may be used in conjunction with any of the sling embodiments described herein.

As previously discussed, the slings can be supplied to the surgeon with the sutures preattached or the sutures can be attached to the suture receiving sites by the surgeon. In either case, a variety of suture attachment methods are contemplated by the present invention.

For example, FIG. 8A shows an enlarged top view of an end portion of a sling having two suture receiving sites 18 with a suture 36 secured thereto. In this embodiment, the suture 36 is looped through the suture receiving sites 18, as illustrated in the cross-sectional view of FIG. 8B. Alternatively, the suture can be threaded through one suture receiving site and out the other suture receiving site without looping through the sling material therebetween.

Alternatively, the suture 36 can be threaded through a single suture receiving site 18 as illustrated in FIGS. 8C and 8D.

Figure 8E:
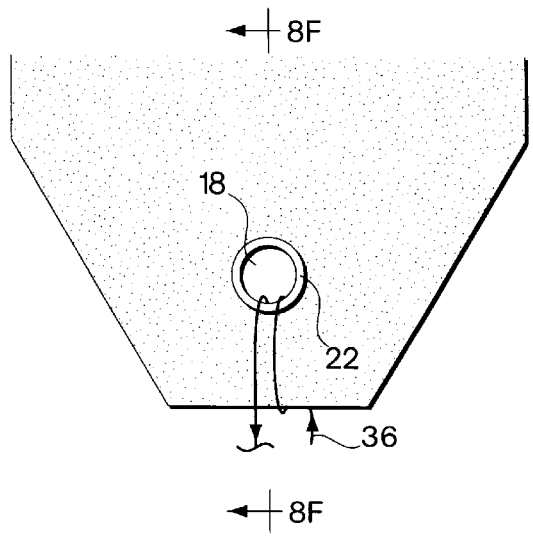
FIG. 8E is an enlarged top view of an end portion of a sling showing a suture looped around the suture receiving site and an edge of the sling.
Figure 8F:
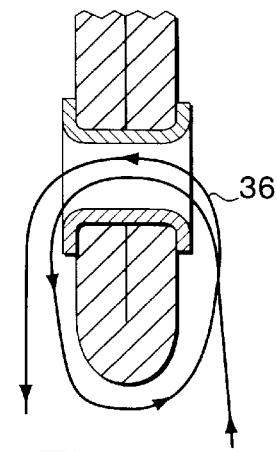
FIG. 8F is a cross-sectional view of the sling taken along line 8F—8F of FIG. 8E.

Another method of attaching the suture to the sling is illustrated in FIGS. 8E and 8F. In accordance with this method, the suture 36 is looped around the suture receiving site 18 and the edge of the sling.

While FIGS. 8A–8E show a variety of methods for attaching the suture to the sling, those skilled in the art will appreciate that other methods may also be used.

Yet another method of attaching the suture 36 utilizes a connector to link the suture to the sling. Suitable connectors for linking the suture to the sling are disclosed in the copending U.S. patent Application entitled "Method and Apparatus for Minimally Invasive Pelvic Surgery," U.S. patent application Ser. No. 09/023,533 filed simultaneously herewith, and the identically titled U.S. Provisional Patent Application Ser. No. 60/038,380 filed Feb. 13, 1997, the disclosures of which are incorporated herein by reference. In such embodiments, the sling has a ring member therein to permit the connector to be attached to the sling. Ring members suitable for attaching the connector are also disclosed in the above incorporated copending U.S. patent Application entitled "Method and Apparatus for Minimally Invasive Pelvic Surgery," U.S. patent application Ser. No. 09/023,533 filed simultaneously herewith, and the identically titled U.S. Provisional Patent Application Ser. No. 60/038,380 filed Feb. 13, 1997.

Those skilled in the art will appreciate that a variety of other suture attachment methods can be used in accordance with the present invention.

The present invention also includes prefabricated slings having integral attachment members 148. Such slings can be die cut or ultrasonically cut out of a solid sheet of biocompatible material. Preferably, the slings having integral attachment members are cut from one length of material and the edges are heat sealed. Alternatively, the integral attachment members may comprise trailing filaments such as longer strands in a woven sling. In a further embodiment, the integral attachment members comprise filaments interwoven through the sling material. The function of the integral attachment members 148 is similar to that of the sutures 36, which allow the surgeon to suspend the sling from a structure, such as the pubic bone as described in more detail below.

Figure 10A:
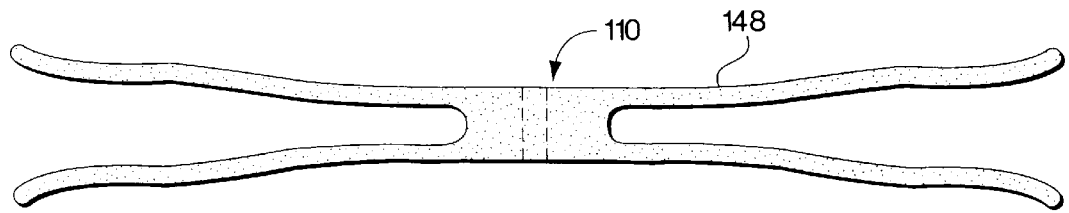
FIG. 10A is a plan view of a generally rectangular shaped sling with bilaterally extending integral attachment members.
Figure 10B:
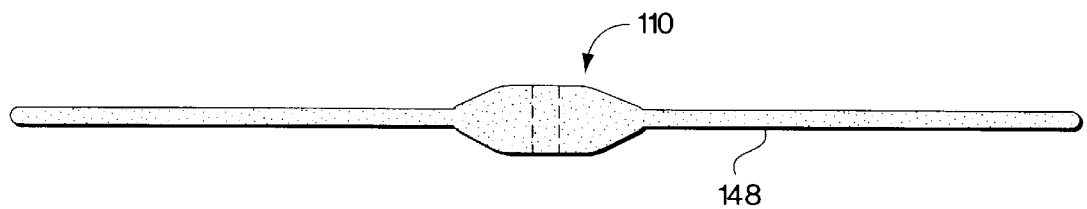
FIG. 10B is a plan view of a generally hexagonal shaped sling with bilaterally extending integral attachment members.

Representative examples of slings having integral attachment members are depicted in FIGS. 10A and 10B. FIG. 10A shows a generally rectangular shaped sling 110 in which bilaterally extending integral attachment members 148 are formed from the same piece of material as the sling. FIG. 10B shows a generally hexagonal shaped sling 110 in which bilaterally extending integral attachment members 148 are formed from the same piece of material as the sling. Those skilled in the art will appreciate that slings with integral attachment members having configurations other than those shown in FIGS. 10A and 10B are also contemplated by the present invention.

The slings of the present invention may be individually packaged and/or sterilized prior to purchase. The packaging may protect the sling during storage. For example, in embodiments in which the sling material comprises a collagen coated filamentous material, the packaging may protect the sling from damage by ultraviolet light. The sling may be soaked in an antibiotic solution, such as a solution of neomycin, bacitracin, or polymixim, to prevent microorganisms from collecting on and colonizing the surface of the sling during manipulation, thereby reducing the risk of infection following implantation of the sling. The sling may also be sterilized by ethylene oxide or irradiation. Uptake and delivery of the antibiotic may be enhanced by using a coated sling as described above.

In embodiments in which the sling is made of natural tissue, the sling may be stored in glutaraldehyde or freeze dried. Prior to use in the surgical procedure, the natural tissue may be preconditioned by soaking the sling in a saline solution, such as any standard commercially available saline solution.

The present invention also includes a stabilization sling kit for maintaining urinary continence. Preferably, the kit comprises a prepackaged sling. More preferably, the kit comprises a sterilized sling. In one embodiment, the kit includes a sling having sutures secured thereto. Alternatively, the sling included in the kit may have integral attachment members as described above.

A minimally invasive percutaneous method of sling delivery and stabilization to treat an incontinent patient will now be described with reference to FIGS. 11–14. Preoperatively, the patient receives broad spectrum antibiotics, such as gentamicin and ampicillin. The patient is placed in the dorsal lithotomy position and regional or general anesthesia is administered. Preparation of the patient emphasizes isolation of the anus with a stapled towel or plastic drape. A Foley catheter is placed.

Figure 12:
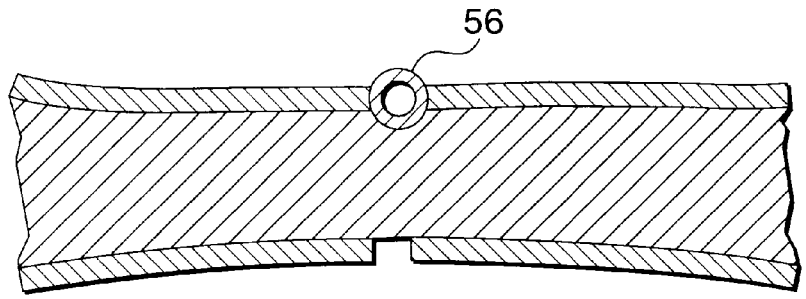
FIG. 12 is a schematic cross-sectional view taken through the urethra and upper vaginal wall illustrating an incision in the upper vaginal wall.
Figure 13:
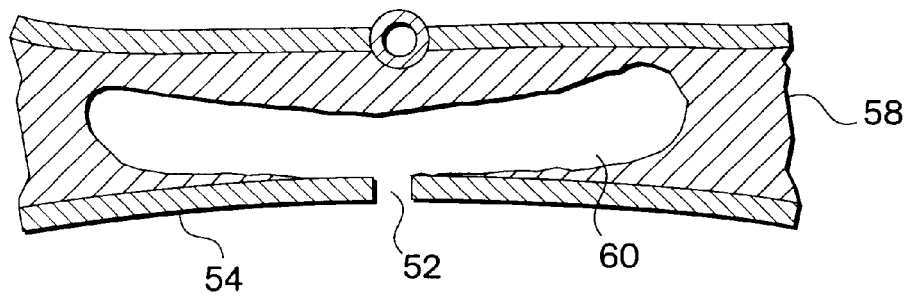
FIG. 13 is a schematic cross-sectional view taken through the urethra and upper vaginal wall illustrating a bilaterally extending pocket created by blunt dissection.

An approximately 1–2 centimeter midline incision 52 is made in the upper vaginal wall 54 beneath the bladderneck, such as at the urethro-vesical junction, as illustrated in FIG. 12. The surgeon then inserts an instrument such as surgical scissors through the incision in the upper vaginal wall and bluntly dissects the tissue 58 on both sides of the urethra 56 to create a bilaterally extending pocket 60, which is illustrated in FIG. 13.

The bilaterally extending pocket can also be created and the sling can be inserted using a variety of other minimally invasive instruments/methods including the transvaginal, hiatal and percutaneous approaches disclosed in the copending U.S. patent application entitled "Transvaginal Anchor Implantation Device," Ser. No. 08/744,439 filed Nov. 8, 1996, the copending U.S. patent Application entitled "Percutaneous and Hiatal Devices and Methods for Use in Minimally Invasive Pelvic Surgery" U.S. patent application Ser. No. 09/023,965 filed simultaneously herewith, the U.S. Provisional Patent Application entitled "Percutaneous and Hiatal Devices and Methods for Use in Minimally Invasive Pelvic Surgery," Ser. No. 60/038,171, filed Feb. 13, 1997, the copending U.S. patent Application entitled "Method and Apparatus for Minimally Invasive Pelvic Surgery" U.S. patent application Ser. No. 09/023,533 filed simultaneously herewith, and the U.S. Provisional Patent Application entitled "Method and Apparatus for Minimally Invasive Pelvic Surgery," Ser. No. 60/038,380, filed Feb. 13, 1997, the disclosures of which are incorporated herein by reference. For example, these other approaches may be employed when the physician desires to attach a long strip of material to the pubic bone or other structures such as the abdominal musculature with a bone anchor or other securing device. In such approaches, an opening capable of accommodating the long strip of material is created in the body tissue, the sling is introduced into the opening in the body tissue, and the sling is attached directly or indirectly to the pubic bone or other structures such as the abdominal musculature.

Either before or after creating the pocket 60, a bone anchor 62, such as a screw in anchor, a push in anchor, or a punch in anchor, is introduced into the pubic bone 64 for fixation of suspensory sutures, with or without pre-drilling a hole in the pubic bone. For instance, the bone anchor is introduced using a bone anchor implantation device of a type such as that illustrated in FIGS. 15–19 of copending U.S. application Ser. No. 08/385,897, filed Feb. 9, 1995, which is hereby incorporated herein by reference. Bone anchor sites are located by placing the bone anchor implantation device on the body over the area of the pubic bone after visualization or digital palpation over the bone. The surgeon then extends the bone probes distally until both probes have made contact with the pubic bone. Preferably, one anchor 62 for each side (two per patient) is implanted into the tubercle portions of the pubic bone 64 (approximately two centimeters lateral to the symphysis pubis). Preferably, the eyelet of the anchor is recessed below the surface of the bone or flush with the surface of the bone. The anchor 62 preferably has a suture 36 slidably secured thereto prior to implantation of the anchor into the pubic bone so that a first suture end and a second suture end extend from the implanted anchor after removal of the anchor driver.

Two separated approximately one inch transverse incisions are made over the pubic bone as illustrated in U.S. Pat. No. 5,611,515, issued Mar. 18, 1997 to Benderev et al., the disclosure of which is incorporated herein by reference, and dissection is carried down to the area of the rectus fascia. The first end of the anchored suture is manually placed into a suture channel of a suture passer of a type such as that illustrated in FIGS. 45 and 45a of the above incorporated U.S. Pat. No. 5,611,515, issued Mar. 18, 1997 to Benderev et al. The probe is moved distally to lock the suture therein.

Beginning on the right side, the suprapubic wound is stretched cephalad to allow the vertical passage of the suture passer through the rectus fascia with the probe tip fully exposed. Distal advancement of the suture passer is accomplished with the tip proximally retracted within the probe guide. The suture passer is acutely angled into the abdomen so that the point rests on the underside of the pubic periosteum.

While maintaining contact with the underside of the pubis, the suture passer with the probe tip retracted is thereafter passed distally toward the introitus. At the completion of this distal passage, the suture passer can be palpated through the introitus to the right of the urethra 56. The distal end tip of the suture passer is withdrawn from the surface of the pubourethral ligament and gently swept along the pubocervical fascia to the area of the bladder neck under the guidance of a finger within the vagina Palpation through the vagina may be safely performed to assist in localization of the suture passer tip.

The probe tip is then distally extended. The suture passer is then passed through the endopelvic fascia and into the pocket 60 between the urethra 56 and the upper vaginal wall 54 at which time the probe tip is retracted. The surgeon then guides the suture passer distally into the vagina through the midline incision 52 in the upper vaginal wall 54. The probe is then retracted maximally to the unlocked position to allow the first end of the suture to be manually removed from the suture channel.

The surgeon selects a sling, such as sling 10 of the present invention. The surgeon secures the suture 36 to a first end portion 14 of the sling by advancing the first end of the suture through the suture receiving site 18 as previously described.

After securing the suture 36 to the first end portion of the sling 10, the first end of the suture is placed into the unlocked suture channel and locked into place. The suture passer and suture locked therein are then pulled up through the suprapubic wound. The first end of the suture is then released from the suture channel by manually retracting the probe.

The identical procedure is performed on the left side.

The surgeon places the sling 10 into the pocket 60 through the midline incision 52 in the upper vaginal wall 54. The sling is placed under the urethra, preferably under the bladderneck, in order to realign the urethra and bladderneck to the correct anatomical position and provide a stable floor to counteract internal stresses.

As will be apparent to one of skill in the art, the sling may be placed beneath the bladderneck in a variety of ways other than via the pocket 60. For instance, an inverted U shaped incision may alternatively be made beneath the bladderneck. The tissue beneath the inverted U shaped incision may be bluntly dissected to create a flap. The sling may then be inserted in the dissected opening.

After placing the sling in the pocket or opening, the surgeon aligns the sling so that the visual indicator 20 is located directly beneath the urethra 56. As will be apparent to one of skill in the art, alignment of the sling relative to the urethra can be accomplished in a variety of ways, such as by direct visualization.

Figure 11:
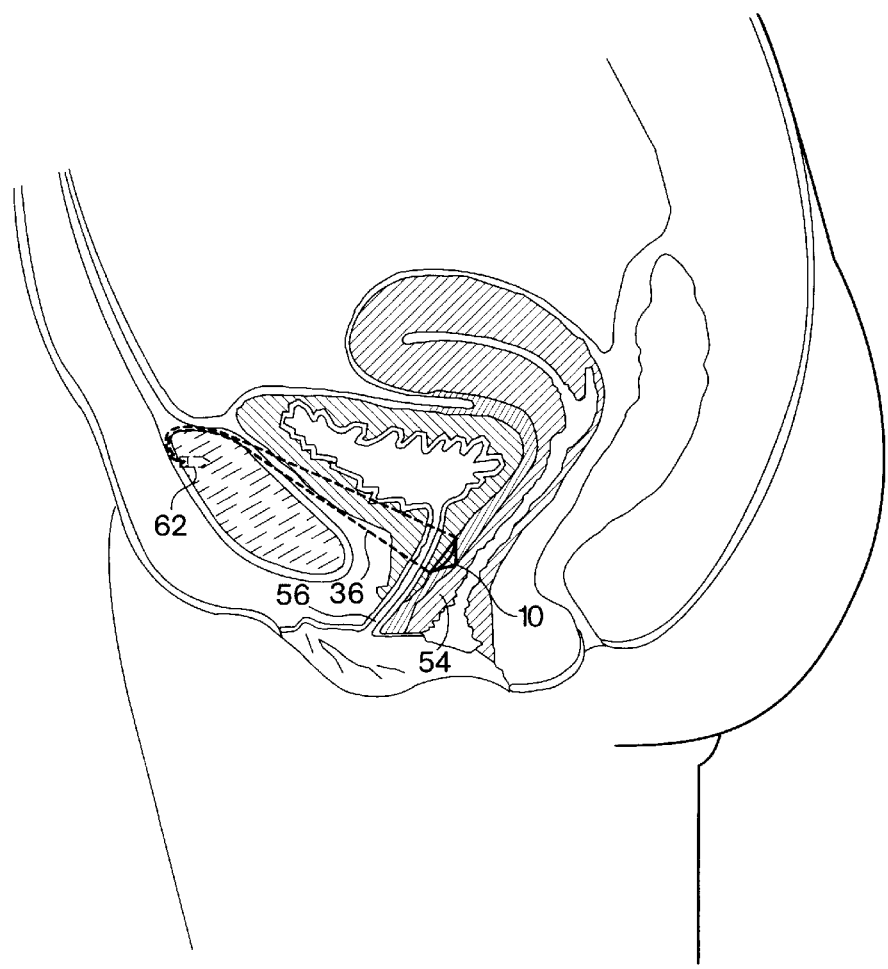
FIG. 11 is a sagittal section of a female pelvis illustrating the location of the sling of the present invention relative to the bladder neck and the pubic bone.
Figure 14:
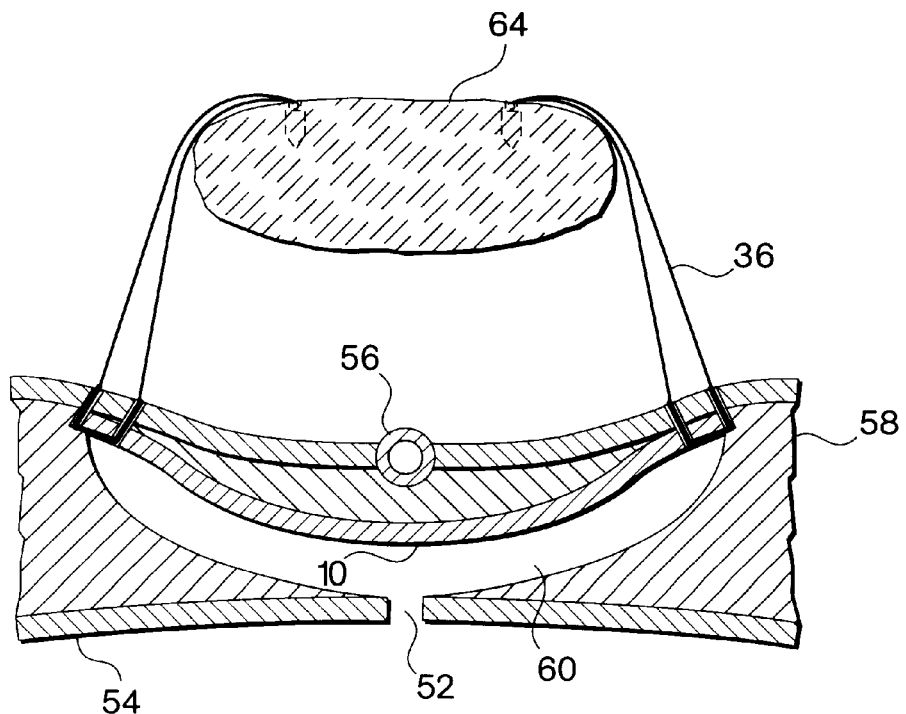
FIG. 14 is a schematic view of a sling of the present invention positioned in the pocket of FIG. 13, the sling being suspended from sutures secured to a bone anchor implanted in the pubic bone.

After the sling 10 is correctly positioned, the first and second ends of the suture on each side are tied to each other with sufficient tension to stabilize and support the bladder neck as illustrated in FIGS. 11 and 14. The Foley catheter is removed prior to tying the suspensory sutures.

In order to minimize postoperative urinary blockage caused by excessive tension, and minimize postoperative urinary incontinence due to insufficient tension, suture tension is regulated by tying the first and second ends of the sutures across a suture tensioner of a type such as that illustrated in FIGS. 46–49 of the above incorporated U.S. patent application entitled "Bladder Neck Suspension Procedure", Ser. No. 08/042,739, filed Apr. 5, 1993. The suture tensioner is thereafter removed and the position of the visual indicator 20 relative to the urethra is reconfirmed prior to closing the vaginal and suprapubic wounds.

The wounds are irrigated with an antibiotic solution, such as a bacitracin solution. The wound edges and the rectus fascia at the suture entry points are infiltrated with bupivacaine. A Foley catheter is introduced. Alternatively, a suprapubic tube can be placed, especially in those patients having dexterity problems or an aversion to learning intermittent catheterization.

Following surgery, the patient is given either ciprofloxacin or ofloxacin for ten days. For those patients having a Foley catheter, the catheter is removed approximately one week following surgery. The patient performs intermittent catheterization as necessary until the post-void residuals are less than 75 cc on two consecutive catheterizations. In patients having a suprapubic tube, the suprapubic tube is removed when the post-void residuals are less than 75 cc following two consecutive urinations.

As will be apparent to one of skill in the art, the foregoing method can be readily modified for use with sling 110 in which the function of the integral attachment members 148 is similar to that of the sutures 36 described above. In addition, while the foregoing procedure was described using two bone anchors per patient, one of ordinary skill in the art will recognize that the procedure could also be accomplished using either one anchor per patient or greater than two anchors per patient. The one anchor embodiment is especially preferred for use with slings having a single suture end or single integral attachment member extending from each end of the sling, such as the sling 110 illustrated in FIG. 10B. In those cases where one anchor per patient is used, the anchor is preferably located adjacent to the symphysis pubis. The slings of the present invention can also be suspended from structures other than bone, such as Cooper's ligament or the rectus fascia without using bone anchors.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A sling for improving urinary continence comprising:
    a length of biocompatible material, having central portion positioned between a first end portion and a second end portion, and a longitudinal central axis extending between said first and second end portions;
    at least one pair of preformed suture receiving sites, wherein each pair of suture receiving sites comprises a first suture receiving site disposed in said first end portion of said material and a second suture receiving site disposed in said second end portion of said material; and
    a visual indicator extending across the central portion of said material.

2. A sling as in claim 1, having an odd number of suture receiving site pairs, greater than one, wherein one of said suture receiving site pairs is disposed along said longitudinal central axis extending between said first and second end portions; and the remainder of said suture receiving site pairs are disposed symmetrically about said longitudinal central axis extending between said first and second end portions.

3. A sling as in claim 1, having an even number of suture receiving site pairs in each end portion, wherein all of said suture receiving site pairs are disposed symmetrically about said longitudinal central axis extending between said first and second end portions.

4. A sling as in claim 1, wherein said visual indicator comprises a radiopague material.

5. A sling as in claim 1, wherein said biocompatible material comprises directionally ordered filaments, grains, striations, or polymeric chains.

6. A sling as in claim 5, wherein said suture receiving sites are disposed in a cross grain section which is produced by folding over the edges of said first and second end portions of said directionally ordered biocompatible material.

7. A sling as in claim 6, wherein the folded edges of said end portions are secured by a technique selected from the group consisting of sewing, heat sealing, ultrasonic sealing, stapling, and gluing.

8. A sling as in claim 7, wherein said biocompatible material is woven.

9. A sling as in claim 8, further comprising at least one attachment member extending laterally from said end potion, said attachment member being formed from trailing fibers of the woven biocompatible material.

10. A sling as in claim 1, wherein said biocompatible material is derived from animal tissue.

11. A sling as in claim 1, wherein said biocompatible material derived from animal tissue is selected from the group consisting of striated muscle, fascia lata, rectus fascia, dura, pericardium, and processed collagen.

12. A sling as in claim 1, wherein said biocompatible material is bioabsorbable.

13. A sling as in claim 1, wherein said biocompatible material is covered with a bioabsorbable coating.

14. A sling as in claim 13, wherein said bioabsorbable coating is selected from the group consisting of collagen, gelatin, polyvinyl alcohol, polyvinyl pyrrolidine, polyglycolic acid, and polylactic acid.

15. A sling as in claim 1, wherein said biocompatible material is impregnated with an antibiotic.

16. A sling as in claim 1, further comprising a stabilizer for strengthening and reducing bucking of said sling, said stabilizer being disposed in said at least one of said first and second end portions of said sling.

17. A sling as in claim 1, wherein said suture receiving sites are reinforced.

18. A sling of as in claim 17, wherein said suture receiving sites are reinforced by ultrasonic sealing or heat sealing.

19. A sling of as in claim 17, wherein said suture receiving sites are reinforced with an eyelet.

* * * * *

UNITED STATES PATENT AND TRADEMARK OFFICE
CERTIFICATE OF CORRECTION

PATENT NO.   : 6,042,534
DATED        : March 28, 2000
INVENTOR(S)  : Barry N. Gellman, William Martin and Raymond Rackley It is certified that error appears in the above-identified patent and that said Letters Patent is hereby corrected as shown below:

Claim 1 is amended as follows:

1. A sling for improving urinary continence comprising:

length of biocompatible material, having a central portion positioned between a first end portion and a second end portion, and a longitudinal central axis extending between said first and second end portions;

at least one pair of preformed suture receiving sites, wherein each pair of suture receiving sites comprises a first suture receiving site disposed in said first end portion of said material and a second suture receiving site disposed in said second end portion of said material; and a visual indicator extending across the central portion of said material.

Signed and Sealed this

Twenty-first Day of May, 2002

*Attest:*

*Attesting Officer*

JAMES E. ROGAN
*Director of the United States Patent and Trademark Office*